(12) United States Patent
Smouse

(10) Patent No.: US 9,168,162 B2
(45) Date of Patent: Oct. 27, 2015

(54) METHODS AND APPARATUS FOR TREATING A TYPE 2 ENDOLEAK FROM WITHIN AN ENDOLUMINAL STENT

(71) Applicant: Harry Robinson Smouse, Peoria Heights, IL (US)

(72) Inventor: Harry Robinson Smouse, Peoria Heights, IL (US)

(73) Assignee: Elgco, LLC, Peoria Heights, IL (US)

( * ) Notice: Subject to any disclaimer, the term of this patent is extended or adjusted under 35 U.S.C. 154(b) by 192 days.

(21) Appl. No.: 13/679,376

(22) Filed: Nov. 16, 2012

(65) Prior Publication Data

US 2013/0131776 A1    May 23, 2013

Related U.S. Application Data

(60) Provisional application No. 61/560,929, filed on Nov. 17, 2011.

(51) Int. Cl.
| | |
|---|---|
| *A61F 2/95* | (2013.01) |
| *A61F 2/07* | (2013.01) |
| *A61B 17/064* | (2006.01) |
| *A61B 17/068* | (2006.01) |

(52) U.S. Cl.
CPC .............. *A61F 2/95* (2013.01); *A61B 17/0642* (2013.01); *A61B 17/0682* (2013.01); *A61F 2/07* (2013.01); *A61B 2017/0641* (2013.01); *A61F 2002/077* (2013.01)

(58) Field of Classification Search
CPC .................. A61B 17/0682; A61B 2017/0641; A61F 2/07; A61F 2/95; A61F 2250/0069; A61F 2002/077; A61F 2002/823

USPC ............ 600/200; 606/191, 192, 194; 623/1.1, 623/1.3, 1.23
See application file for complete search history.

(56) References Cited

U.S. PATENT DOCUMENTS

| | | |
|---|---|---|
| 6,475,466 B1 | 11/2002 | Ricci et al. |
| 6,699,186 B1 | 3/2004 | Wolinsky et al. |
| 6,743,173 B2 | 6/2004 | Penner et al. |
| 6,773,454 B2 | 8/2004 | Wholey et al. |
| 6,840,956 B1 | 1/2005 | Wolinsky et al. |
| 7,105,031 B2 | 9/2006 | Letort |
| 7,727,199 B2 | 6/2010 | Fernandes et al. |
| 7,993,386 B2 | 8/2011 | Elliott |
| 8,003,122 B2 | 8/2011 | Zhao |
| 8,048,145 B2 | 11/2011 | Evans et al. |

(Continued)

OTHER PUBLICATIONS

International Search Report and Written Opinion for PCT/US12/65513, mailed on Mar. 12, 2013, 13 pages.

*Primary Examiner* — Jonathan W Miles
*Assistant Examiner* — George J Ulsh
(74) *Attorney, Agent, or Firm* — Cooley LLP

(57) ABSTRACT

A repair device includes a first elongate member, a second elongate member, and a seal member. The first elongate member includes a proximal end portion and a distal end portion and defines a lumen therebetween. The second elongate member includes a proximal end portion and a distal end portion and is movably disposed within the lumen. The distal end portion of the second elongate member is configured to puncture an endoluminal stent graft disposed within an artery of a patient and to be inserted, at least partially, into an aneurysm sac. The seal member is releasably coupled to the distal end portion of the first elongate member. The seal member is configured to be coupled to the endoluminal stent graft to seal an opening formed by the distal end portion of the second elongate member.

12 Claims, 24 Drawing Sheets

(56) References Cited

U.S. PATENT DOCUMENTS

| | | |
|---|---|---|
| 8,118,856 B2 | 2/2012 | Schreck et al. |
| 8,128,680 B2 | 3/2012 | Arnault De La Menardiere et al. |
| 8,182,525 B2 | 5/2012 | Herbowy et al. |
| 8,262,686 B2 | 9/2012 | Fogarty et al. |
| 8,317,823 B2 | 11/2012 | Pavcnik et al. |
| 8,377,110 B2 | 2/2013 | Douglas et al. |
| 2002/0169497 A1 | 11/2002 | Wholey et al. |
| 2003/0014075 A1 | 1/2003 | Rosenbluth et al. |
| 2003/0051735 A1* | 3/2003 | Pavcnik et al. ............... 128/831 |
| 2003/0109820 A1 | 6/2003 | Gross et al. |
| 2004/0059406 A1 | 3/2004 | Cully et al. |
| 2005/0004660 A1 | 1/2005 | Rosenbluth et al. |
| 2005/0090804 A1 | 4/2005 | Chobotov et al. |
| 2005/0182290 A1 | 8/2005 | Lau et al. |
| 2005/0245891 A1 | 11/2005 | McCormick et al. |
| 2006/0264368 A1 | 11/2006 | Ganesan et al. |
| 2007/0150041 A1 | 6/2007 | Evans et al. |
| 2007/0282423 A1 | 12/2007 | DiCarlo |
| 2008/0221600 A1 | 9/2008 | Dieck et al. |
| 2008/0228259 A1 | 9/2008 | Chu |
| 2008/0275536 A1 | 11/2008 | Zarins et al. |
| 2008/0294237 A1 | 11/2008 | Chu |
| 2009/0287145 A1 | 11/2009 | Cragg et al. |
| 2010/0030255 A1 | 2/2010 | Berra et al. |
| 2010/0198329 A1 | 8/2010 | Kassab et al. |
| 2011/0213364 A1 | 9/2011 | Davis et al. |
| 2011/0213413 A1* | 9/2011 | Brown et al. ............... 606/213 |
| 2011/0245862 A1 | 10/2011 | Dieck et al. |
| 2011/0286925 A1 | 11/2011 | Lerouge et al. |
| 2012/0029610 A1 | 2/2012 | Shaolian et al. |
| 2012/0046684 A1 | 2/2012 | Evans et al. |
| 2012/0109279 A1 | 5/2012 | Mayberry et al. |
| 2012/0150274 A1 | 6/2012 | Shalev et al. |
| 2012/0165917 A1 | 6/2012 | Schreck et al. |
| 2012/0179193 A1 | 7/2012 | Cohn et al. |
| 2012/0184982 A1 | 7/2012 | Herbowy et al. |
| 2012/0185036 A1 | 7/2012 | Arnault De La Menardiere et al. |
| 2012/0265287 A1 | 10/2012 | Sharma et al. |
| 2012/0296413 A1 | 11/2012 | Arbefeuille et al. |

\* cited by examiner

METHODS AND APPARATUS FOR TREATING A TYPE 2 ENDOLEAK FROM WITHIN AN ENDOLUMINAL STENT

CROSS-REFERENCE TO RELATED APPLICATIONS

This application claims priority to and the benefit of U.S. Provisional Patent Application Ser. No. 61/560,929, entitled "Methods and Apparatus for Treating a Type 2 Endoleak within an Endoluminal Stent Graft," filed Nov. 17, 2011, the disclosure of which is incorporated by reference herein in its entirety.

BACKGROUND

The embodiments described herein relate to apparatus and methods for treating leaks within a stent graft. More particularly, the embodiments described herein relate to apparatus and methods for treating a type 2 endoleak from within an endoluminal stent graft.

Abdominal aortic aneurysms (AAA) are a common form of cardiovascular disease and often treated with an endoluminal stent graft. Such known treatments include inserting a catheter into the femoral artery of a patient and placing an endoluminal stent graft (also referred to herein as an "ELG") at the location of the aneurysm. Once in place, the ELG is expanded, creating a snug fit with the aortic walls above and below the aneurysm. In such known procedures, the ELG relieves the pressure on the weakened arterial walls at the location of the aneurysm.

In some instances, endoluminal stent grafts can develop leaks such that blood flow leaks through a given portion of the ELG and into the aneurysm sac (e.g., a type 1 endoleak). In some instances, the aneurysm sac may remain pressurized from blood flowing into the sac from the lumbar or inferior mesenteric arteries even though the ELG has been placed successfully and remains intact without holes or leaks at the seal points (e.g., a type 2 endoleak). Type 2 endoleaks occur when blood flow takes a circuitous route traveling through branches from the non-stented portion of the aorta through anastomotic connections into collateral vessels with a direct communication with the aneurysmal sac. Blood can then travel in a retrograde direction in these collateral vessels, eventually emptying into the sac behind the stent-graft. These collateral vessels, prior to aortic exclusion via the stent-graft, carry blood from the aorta to nutrient beds of lower pressure. When the aorta from which they originate is excluded, the pressure gradient favors flow in the opposite direction.

In such instances, the aneurysm sac can grow in size and thus, the chance for rupture and internal bleeding exists. Known treatments for sealing endoleaks exist and vary with the type and severity of the endoleak. For example, translumbar embolization is a known treatment for type 2 endoleaks. Such procedures require the precise puncture of the aneurysm sac at the endoleak location. More specifically, image guidance techniques are used to guide a needle during insertion through the back of a patient to the aneurysm location. Once at the target location, the position of the needle is verified and the aneurysm sac is punctured. With the aneurysm sac punctured, the needle is positioned at the endoleak location and an embolic agent can be injected into the aneurysm sac to seal the endoleak. Another method of treating a type 2 endoleak is using an endovascular technique, which involves threading a catheter through the connecting arteries that supply blood flow into the aneurysm sac. Once the catheter reaches the sac, the sac and feeding arteries can be embolized sealing the endoleak.

Difficulties of a translumbar embolization procedure include the physician, technician, surgeon, etc., carefully avoiding organs within the body, placing the needle at a precise location to puncture the aneurysm sac, and embolizing at a precise location of the endoleak while carefully avoiding the puncture of the ELG. Difficulties of the endovascular procedure include difficulty threading the catheter through extremely small and tortuous blood vessels in order to reach the blood flow within the aneurysm sac, extremely long procedure times exposing physician and patient to higher radiation doses, and high technical failure rates due to inability to reach the aneurysm sac.

Thus, a need exists for improved apparatus and methods for intra-arterially treating a type 2 endoleak of an ELG.

SUMMARY

Devices and methods for repairing a type 2 endoleak are described herein. In some embodiments, a repair device includes a first elongate member, a second elongate member, and a seal member. The first elongate member includes a proximal end portion and a distal end portion and defines a lumen therebetween. The second elongate member includes a proximal end portion and a distal end portion and is movably disposed within the lumen defined by the first elongate member. The distal end portion of the second elongate member is configured to puncture an endoluminal stent graft disposed within an artery of a patient and to be inserted, at least partially, into an aneurysm sac. The seal member is releasably coupled to the distal end portion of the first elongate member. The seal member is configured to be coupled to the endoluminal stent graft to seal an opening formed by the distal end portion of the second elongate member.

DETAILED DESCRIPTION

Figure 1:
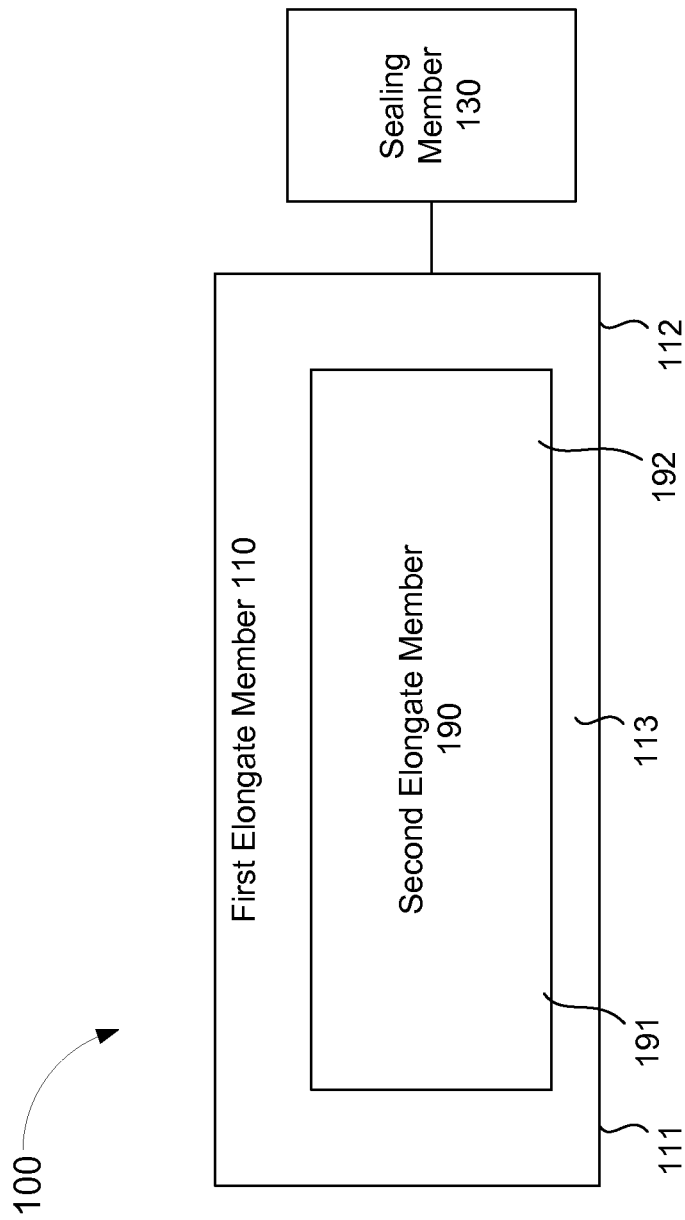
FIG. 1 is a schematic block diagram of an endoleak repair device according to an embodiment.

The embodiments described herein relate to an apparatus that is percutaneously inserted into a patient and further into an existing ELG. The endoleak repair devices described herein can facilitate the sealing of a type 2 endoleak via a minimally invasive intra-arterial technique, thus reducing the likelihood of complications due to alternative treatment methods, such as, for example, the translumbar and endovascular embolization procedures described above.

In some embodiments, a repair device includes a first elongate member, a second elongate member, and a seal member. The first elongate member includes a proximal end portion and a distal end portion and defines a lumen therebetween. The second elongate member includes a proximal end portion and a distal end portion and is movably disposed within the lumen defined by the first elongate member. The distal end portion of the second elongate member is configured to puncture an endoluminal stent graft disposed within an artery of a patient and to be inserted, at least partially, into an aneurysm sac. The seal member is releasably coupled to the distal end portion of the first elongate member. The seal member is configured to be coupled to the endoluminal stent graft to seal an opening formed by the distal end portion of the second elongate member.

In some embodiments, a repair device includes a first elongate member, a second elongate member, a seal member and a coupling member. The first elongate member is configured to be inserted into an artery of a patient. The first elongate member includes a proximal end portion and a distal end portion and defines a lumen therebetween. The second elongate member is disposed within the lumen defined by the first elongate member. The coupling member includes a first coupling portion configured to releasably couple the seal member to the second elongate member and a second coupling portion configured to couple to the seal member to an endoluminal stent graft disposed within the artery of the patient. The second coupling portion is configured to be in a first constrained configuration when disposed within a lumen defined by the seal member and is configured to be in a second configuration when moved outside of the lumen of the seal member. The second coupling portion is configured to couple the seal member to the endoluminal stent graph when in the second biased configuration.

In some embodiments, a method includes inserting a repair device into an artery such that a distal end portion of the repair device is disposed within an endoluminal stent graft implanted within the artery near an aneurysm. The repair device includes a first elongate member that defines a lumen and a second elongate member that is movably disposed within the lumen. The method includes moving the second elongate member distally through a seal member coupled to a distal end portion of the first elongate member such that a distal end of the second elongate member punctures the endoluminal stent graft forming an opening in the endoluminal stent graft and is at least partially disposed within the aneurysm. An agent is injected through a lumen of the second elongate member and into the aneurysm sac. The method further includes coupling the seal member to the endoluminal stent graft to seal the opening formed by the second elongate.

In some embodiments, a method includes inserting a repair device into an artery such that a distal end portion of the repair device is disposed within an endoluminal stent graft implanted within the artery near an aneurysm. The repair device includes a first elongate member that defines a lumen, a second elongate member that is movably disposed within the lumen, and a seal member that is releasably coupled to a distal end portion of the first elongate member with a coupling member. The method includes moving the second elongate member distally relative to the first elongate member such that a coupling portion of the coupling member is moved distally outside of a lumen of the seal member and at least partially through the endoluminal stent graft. The coupling portion is configured to assume a biased configuration when moved outside the lumen of the seal member to couple the seal member to the endoluminal stent graft. The seal member is released from the first elongate member.

As used in this specification, the words "proximal" and "distal" refer to the direction closer to and away from, respectively, a user who would place the device into contact with a patient. Thus, for example, the end of a device being actuated by the user would be the proximal end, while the opposite end of the device would be the distal end of the device.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls can include, for example, multiple portions that are either continuous or discontinuous from each other. A set of walls can also be fabricated from multiple items that are produced separately and are later joined together (e.g., via a weld, an adhesive, or any suitable method).

As used herein, the singular forms "a," "an" and "the" include plural referents unless the context clearly dictates otherwise. Thus, for example, the term "a lumen" is intended to mean a single lumen or a combination of lumens.

FIG. 1 is a schematic block diagram of an endoleak repair device 100 (also referred to herein as "repair device"), according to an embodiment. The repair device 100 includes a first elongate member 110, a second elongate member 190, and a seal member 130. The first elongate member 110 can be any suitable shape, size, or configuration. For example, in some embodiments, the first elongate member 110 can be cylindrical and can have a diameter suitable for insertion into an artery of a patient.

The first elongate member 110 includes a proximal end portion 111 and a distal end portion 112 and defines a lumen 113 therebetween. While not shown in FIG. 1, in some embodiments, the proximal end portion 111 of the first elongate member 110 can be coupled to or at least partially disposed within a handle. In such embodiments, the handle can include any suitable mechanism or feature that can be engaged by a user (e.g., a physician, technician, etc.) to move or otherwise manipulate at least a portion of the first elongate member 110, as described in further detail herein with respect to specific embodiments. The distal end portion 112 of the first elongate member 110 is configured to be inserted into an endoluminal stent graft (ELG) disposed within an artery of a patient, as further described herein.

The first elongate member 110 can be moved between a first configuration in which the first elongate member 110 is substantially linear or straight for insertion within an artery, and a second configuration in which the distal end portion 112 is moved or deflected such that the distal end portion 112 is disposed at an angle or curves away from a remaining portion of the first elongate member 110. For example, in some embodiments, the first elongate member 110 can have a second configuration in which the distal end portion 112 is disposed substantially perpendicular to a remaining portion (e.g., proximal portion 111) of the first elongate member 110.

The second elongate member 190 includes a proximal end portion 191 and a distal end portion 192 and can be movably disposed within the lumen 113 of the first elongate member 110. More specifically, the second elongate member 190 can be movable within the lumen 113 of the first elongate member 110 and used to puncture a wall of the ELG disposed within the artery of the patient. The second elongate member 190 can be any suitable shape, size, or configuration. For example, in some embodiments, the second elongate member 190 can include a cannula and trocar assembly. In such embodiments, the trocar can be configured to move relative to the cannula to puncture the wall of the ELG (not shown in FIG. 1). In other embodiments, the second elongate member 190 can be a cannula that includes a sharpened (e.g., angled) distal end such that the cannula can puncture the wall of the ELG. In this manner, the second elongate member 190 can define a lumen configured to deliver an agent through a portion (e.g., a lumen) of the second elongate member 190 and into, for example, an aneurysm sac, as further described herein. In some embodiments, the second elongate member 190 can be an elongate member with a sharpened distal end that can puncture the wall of the ELG. In such an embodiment, a separate delivery device can be inserted into the lumen 113 of the guide sheath 110 and through an opening formed by the elongate member and used to deliver an agent to an aneurysm sac.

The seal member 130 can be releasably coupled to the distal end portion 112 of the first elongate member 110. For example, in some embodiments, the seal member 130 can be releasably coupled to the distal end portion 112 via one or more coupling members (not shown). In such embodiments, the coupling member(s) can include a first coupling portion that can include, for example, a latch, a clasp, a tab, a threaded coupler, or the like configured to releasably engage a coupling portion (not shown in FIG. 1) of the first elongate member 110. For example, in some embodiments, the first elongate member 110 can include or otherwise house one or more push rods (not shown in FIG. 1) that are movably disposed within lumens defined by the first elongate member 110. The push rods can be releasably coupled to the first coupling portion of the coupling member to releasably couple the seal member 130 to the first elongate member 110.

In some embodiments, coupling member(s) can each include a second coupling portion (not shown in FIG. 1) that is configured to couple the seal member 130 to the wall of the ELG. For example, in some embodiments, the one or more second coupling portions can include a barb, a hook, a biasing member, and/or the like. The second coupling portions can include a distal end that can puncture the ELG and temporarily couple the repair device 110 to the ELG, as described in more detail below. The second coupling portion can have a first configuration in which the second coupling portion is constrained within a lumen defined by the seal member 130, and a second configuration in which the second coupling portion can assume a biased configuration used to couple the seal member 130 to the wall of the ELG. For example, in some embodiments, the second coupling portion can be formed with a shape-memory material and can have a biased coiled configuration. The seal member 130 can be coupled to the wall of the ELG and released from the first elongate member 110 to seal an opening formed by the distal end portion 192 of the second elongate member 190 as described above and as further described herein.

In some embodiments, the seal member 130 can include a valve configured to receive the distal end portion 192 of the second elongate member 190. For example, in some embodiments, the seal member 130 and the second elongate member 190 can be aligned such that when the second elongate member 190 is moved in a distal direction to puncture the wall of the ELG, the second elongate member 190 can engage the valve to move the valve to an open configuration, thereby allowing at least a portion of the second elongate member 190 to pass through the seal member 130. In some embodiments, the seal member 130 and the second elongate member 190 can be coaxial.

In some embodiments, the repair device 100 can be used to deliver, for example, a sealing agent into an aneurysm sac to repair a type 2 endoleak. In such embodiments, the first elongate member 110 can be inserted into an artery of the patient and guided into a desired position within an ELG. For example, in some embodiments, the first elongate member 110 can be positioned such that the distal end portion 112 is disposed within the ELG. In some embodiments, the distal end portion 112 can be guided within the artery and/or the ELG (e.g., via fluoroscopy or the like) such that the seal member 130 is disposed adjacent to a wall of the ELG. In some embodiments, a user can engage the first elongate member 110 to cause the distal end portion 112 to deflect (e.g., bend, move, or otherwise reconfigure) relative to a longitudinal centerline of the first elongate member 110 to place the seal member 130 adjacent to the wall of the ELG. For example, in some embodiments, the distal end portion 112 of the first elongate member 110 can deflect such that the seal member 130 is disposed substantially perpendicular to the wall of the ELG.

With the seal member 130 disposed adjacent to the wall of the ELG, the second elongate member 190 can be moved in a distal direction such that the distal end portion 192 of the second elongate member 190 punctures the wall of the ELG (as described above). For example, in some embodiments, the second elongate member 190 includes a cannula that can be advanced to the distal end portion 112 of the first elongate member 110 and a trocar movably disposed within a lumen of the cannula can be moved in a distal direction relative to the cannula such that a sharp distal tip of the trocar punctures the wall of the ELG. In other embodiments, the second elongate member 190 can include a sharpened distal end portion 192 configured to puncture the wall of the ELG. In some embodiments, at least a portion of the second elongate member 190 can be configured to pass through a valve (not shown in FIG. 1) of the seal member 130 as described above. In this manner, the valve can be moved to its open configuration to allow the distal end portion 192 of the second elongate member 190 to puncture the wall of the ELG and form an opening in the wall of the ELG. A sealing agent can then be delivered into the aneurysm sac as described below.

As described above, the sealing agent can be delivered through a lumen of the second elongate member 190. For example, as described above, the second elongate member 190 can include a cannula and a trocar movably disposed within the cannula. After puncturing the wall of the ELG, the trocar can be retracted or removed from the cannula and the lumen 113 of the guide sheath 110. The sealing agent can then be delivered through the cannula of the second elongate member 190. With the sealing agent delivered to the aneurysm sac, the seal member 130 can be positioned relative to ELG to seal the opening formed by the second elongate member 190. In some embodiments, the retraction of the second elongate member 190 (e.g., the proximal movement of the second elongate member 190) can be such that as the second elongate member 190 is moved to a proximal position relative to the seal member 130, the valve can return to a closed configuration.

With the seal member 130 disposed in a desired position relative to the opening in the ELG, the seal member 130 can be coupled to the ELG and can be released from the first elongate member 110. For example, in some embodiments, the second coupling portion of the seal member 130 can be advanced through the wall of the ELG to couple the seal member 130 thereto. For example, the second coupling portion can be advanced through the wall of the ELG and assume its second configuration to engage an outer surface of the ELG, thereby coupling the seal member 130 to the ELG. The seal member 130 can be decoupled from the first elongate member 110 and the first elongate member 110 can be moved in the proximal direction to remove the first elongate member 110 from the artery. Thus, the type 2 endoleak can be repaired from within the endoluminal graft.

Figure 7:
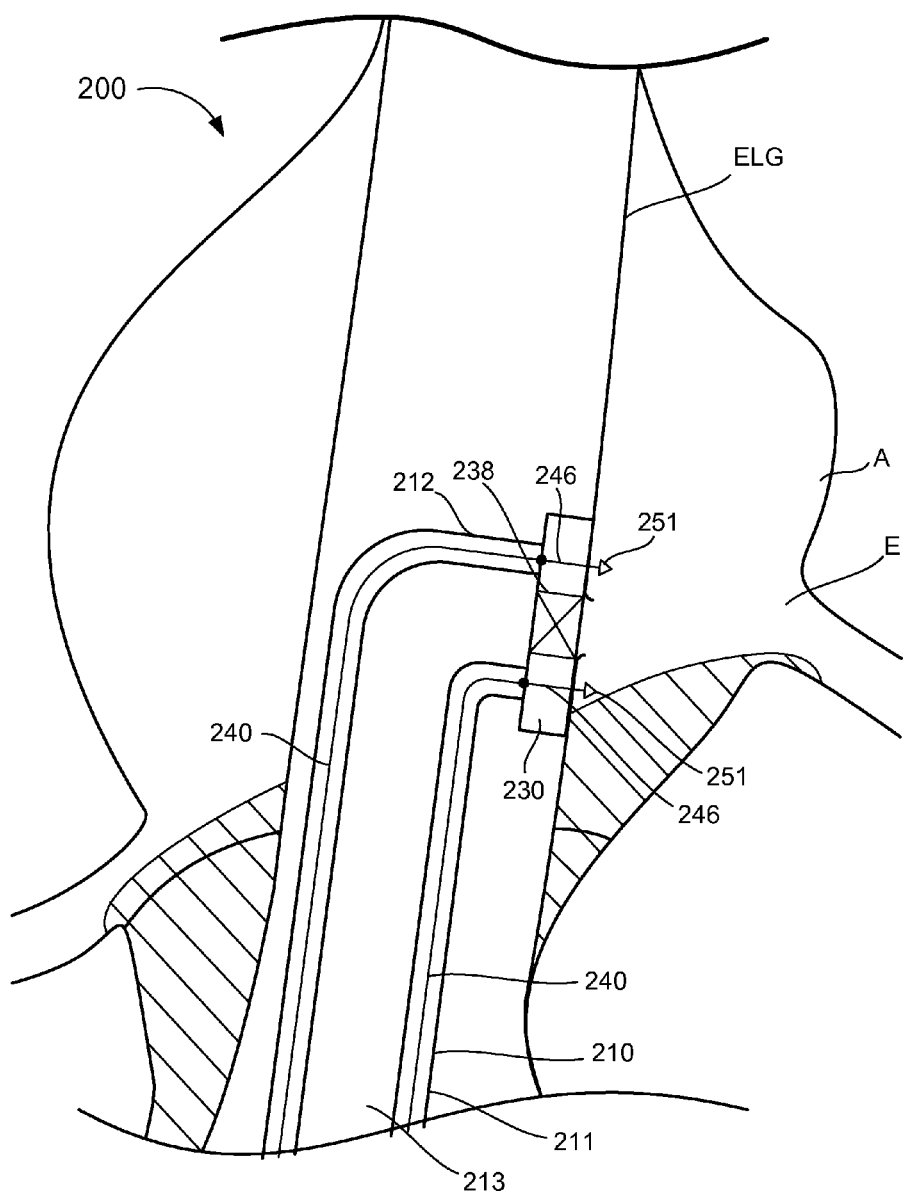
FIG. 7 is a schematic illustration of the endoleak repair device of FIG. 2 in use within the endoluminal graft, in a fourth configuration.
Figure 8:
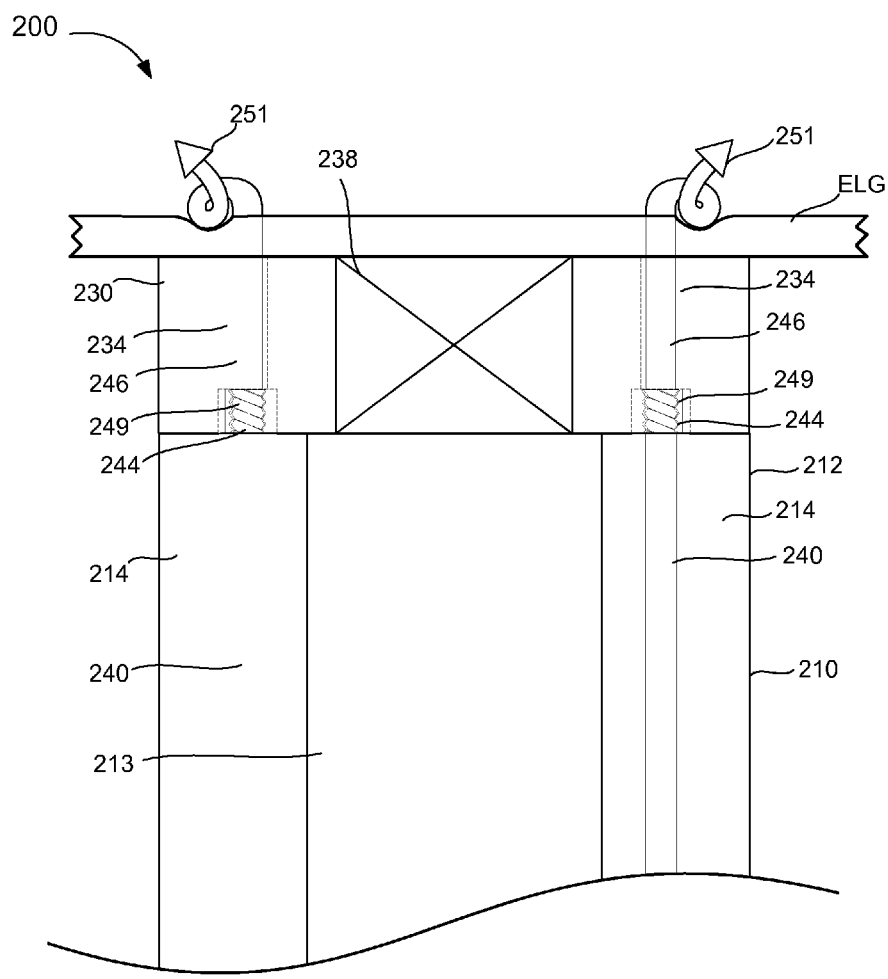
FIG. 8 is an enlarged schematic illustration of a portion of the endoleak repair device of FIG. 2, in the fourth configuration.
Figure 9:
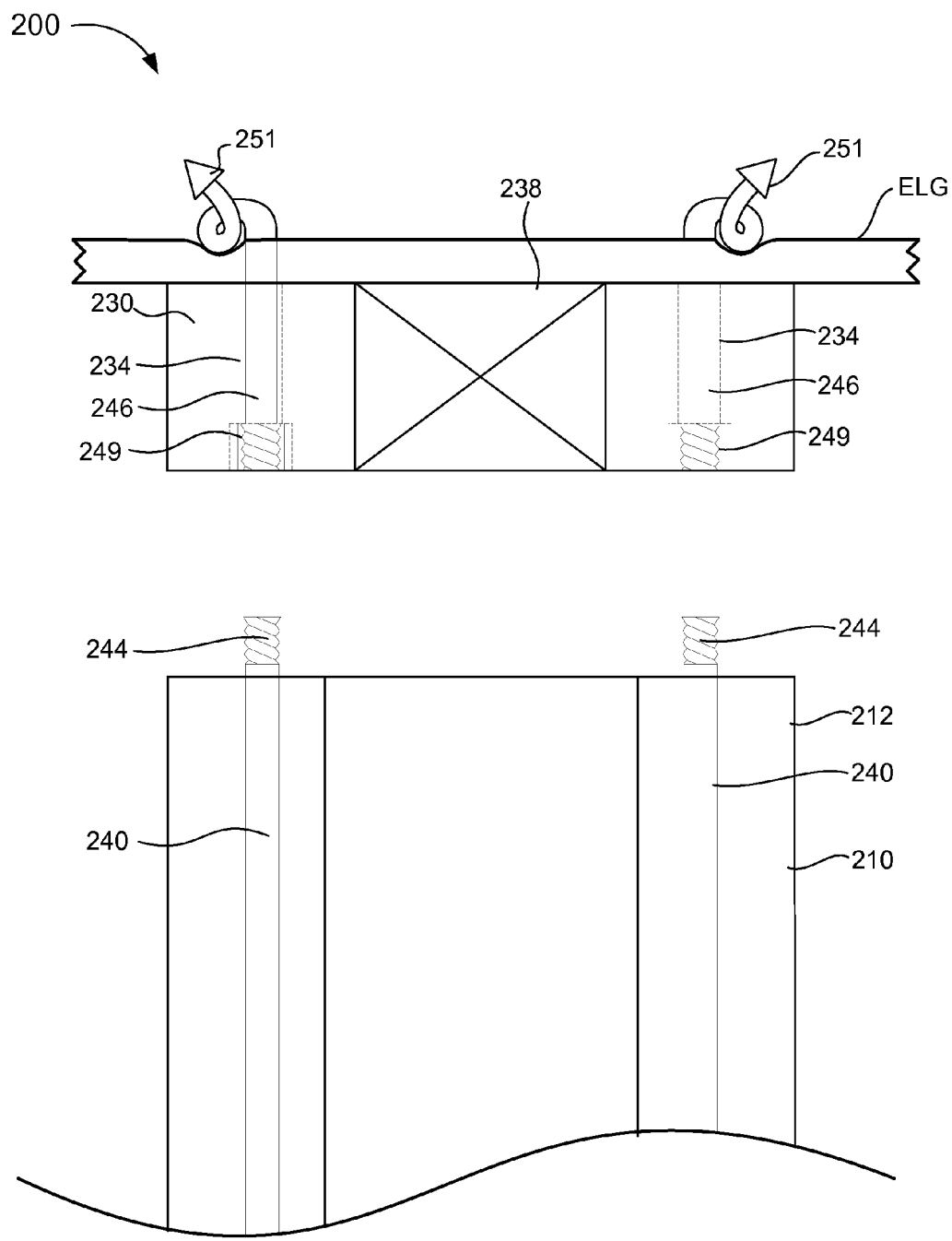
FIG. 9 is a schematic illustration of a portion of the endoleak repair device of FIG. 2, in a fifth configuration.
Figure 10:
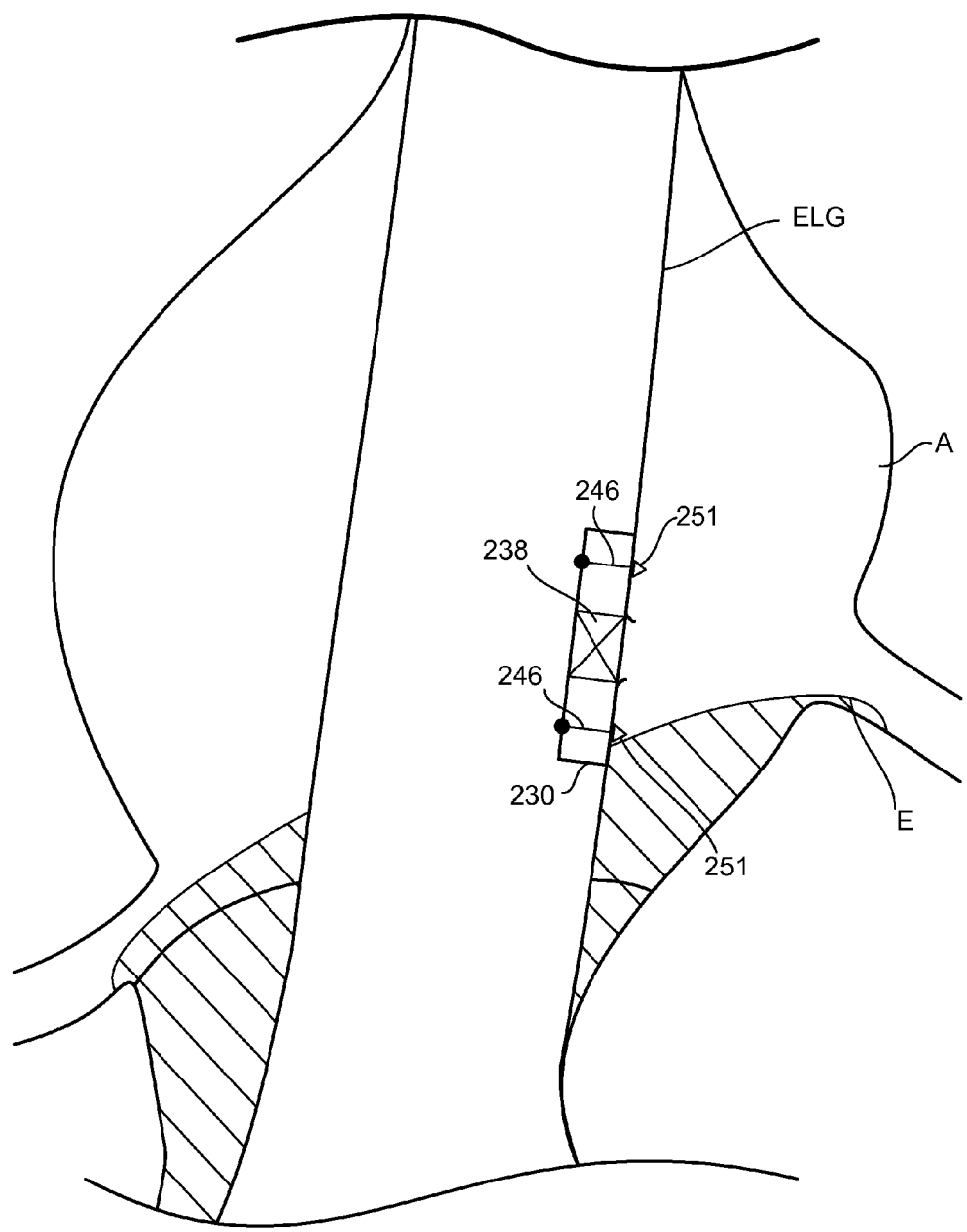
FIG. 10 is a schematic illustration of a seal member included in the endoleak repair device of FIG. 2, in use within the endoluminal graft.

FIGS. 2-10 illustrate a schematic representation of an endoleak repair device 200, according to an embodiment. The endoleak repair device 200 (also referred to herein as "repair device") includes a deformable guide sheath 210 (also referred to herein as "guide sheath 210"), a detachable seal member 230, a set of push rods 240, a cannula 290, and a trocar 295. As described in further detail herein, the repair device 200 can be moved between a first configuration (FIGS. 2-4), a second configuration (FIG. 5), a third configuration (FIG. 6), a fourth configuration (FIGS. 7 and 8), and a fifth configuration (FIGS. 9 and 10).

Figure 4:
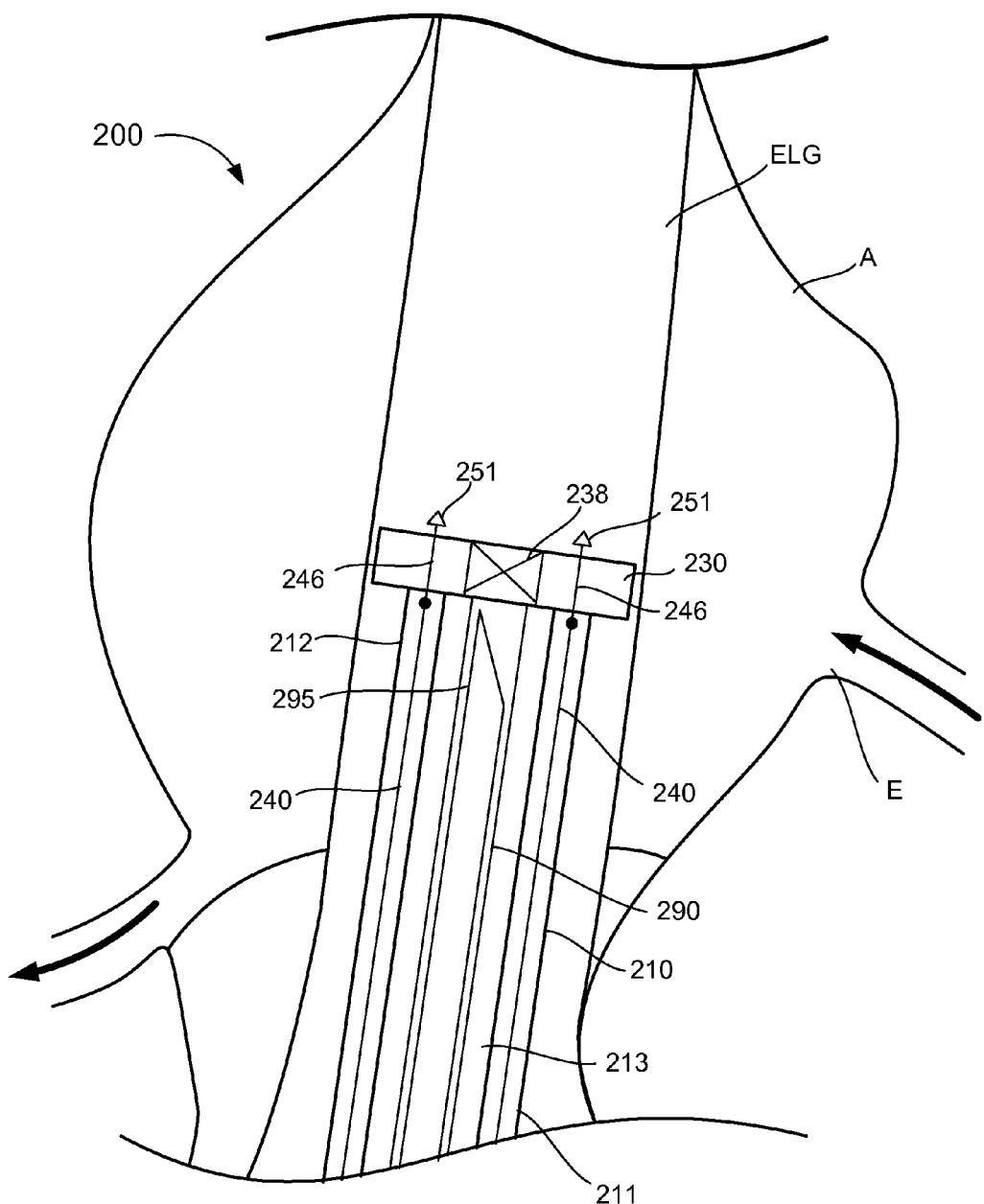
FIG. 4 is a schematic illustration of the endoleak repair device of FIG. 2 in use within an endoluminal graft, in the first configuration.
Figure 5:
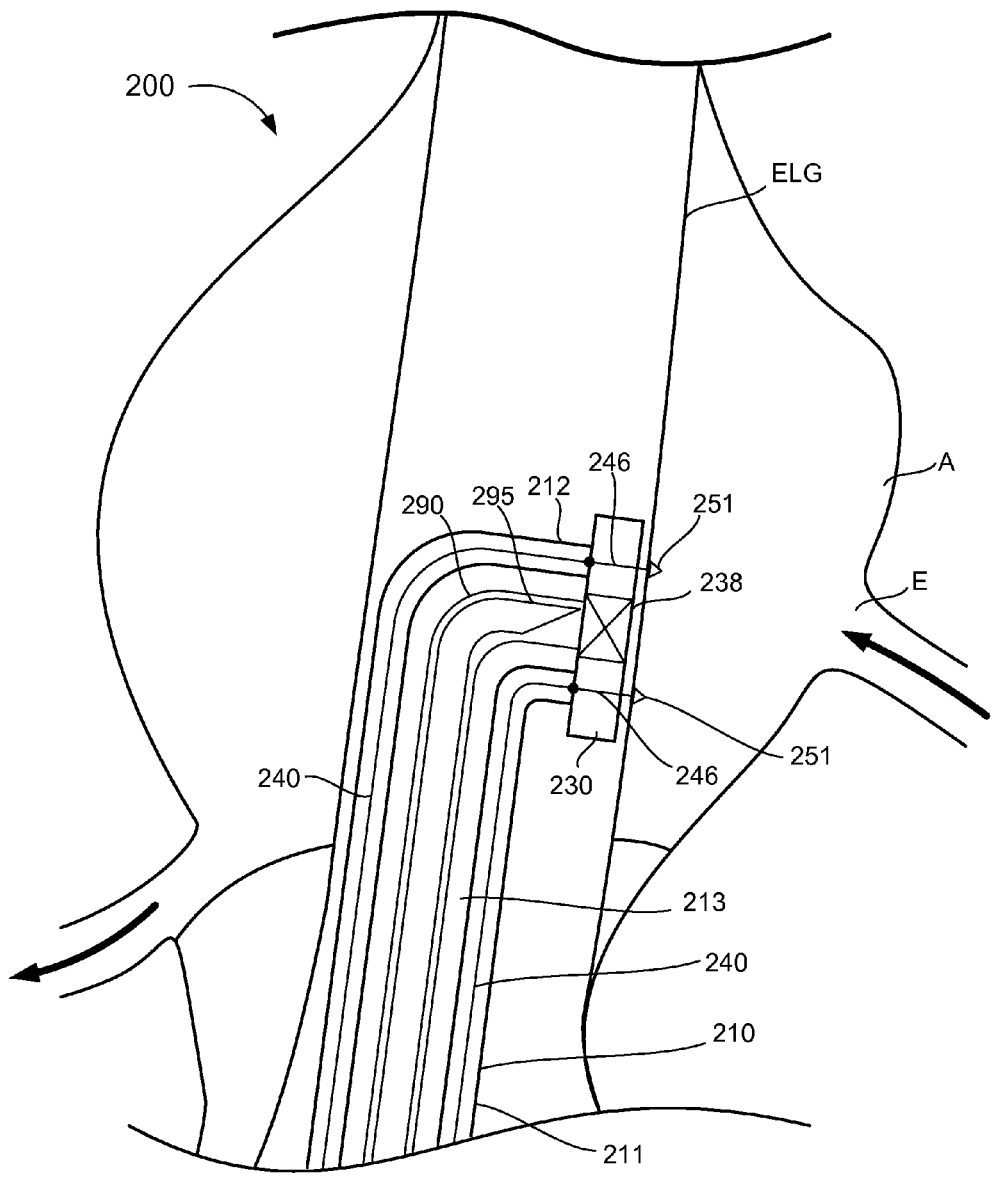
FIG. 5 is a schematic illustration of the endoleak repair device of FIG. 2, in use within the endoluminal graft, in a second configuration.

The guide sheath 210 includes a proximal end portion 211 and a distal end portion 212 and defines a lumen 213, and a set of secondary lumen 214 therebetween. As described in further detail herein, the distal end portion 212 of the guide sheath 210 is configured to deflect (e.g., bend, move, deform, or otherwise reconfigure) between at least a first configuration (FIGS. 2-4) and a second configuration (FIG. 5). The proximal end portion 211 of the guide sheath 210 can be coupled to and/or otherwise disposed within a handle 260 or other suitable device. For example, in some embodiments, the proximal end portion 211 of the guide sheath 210 can be coupled to the handle 260 and the handle 260 can include a port configured to receive the cannula 290 and trocar 295. In this manner, the cannula 290 and the trocar 295 can be inserted into the port and disposed within the lumen 213 of the guide sheath 210. Furthermore, in some embodiments, the handle 260 can include a mechanism or feature configured to actuate the guide sheath 210 to deflect, move, or otherwise manipulate the guide sheath 210, as further described herein. The distal end portion 212 of the guide sheath 210 is coupled to the detachable seal member 230 (also referred to herein as "seal member 230"), as described in further detail herein.

Figure 2:
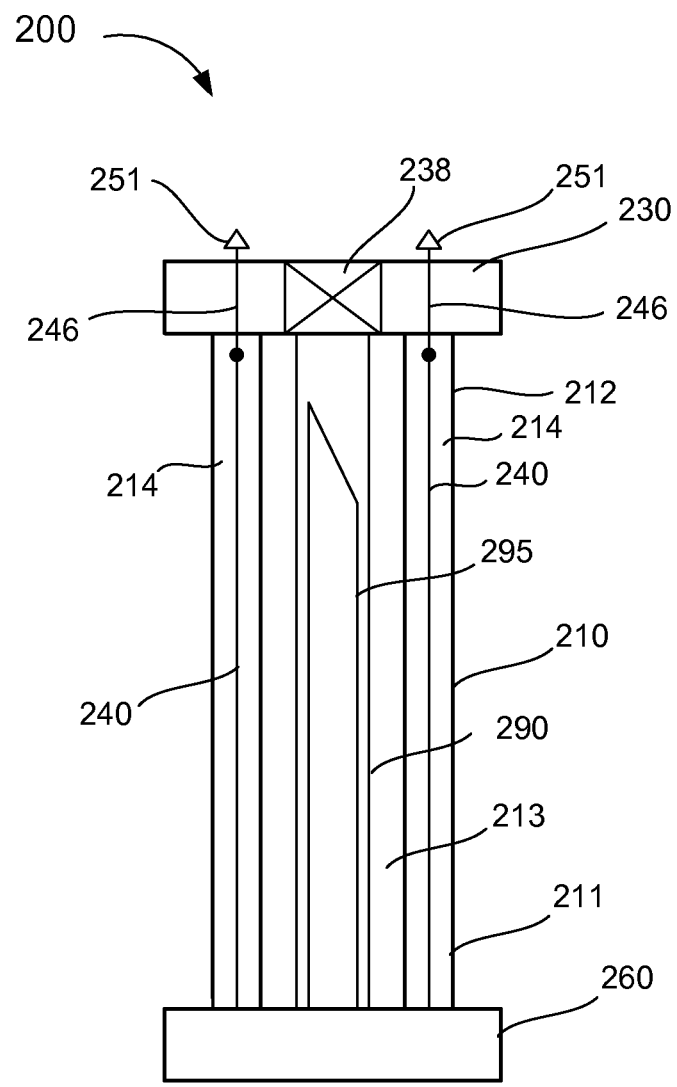
FIG. 2 is a schematic illustration of an endoleak repair device in a first configuration, according to an embodiment.
Figure 3:
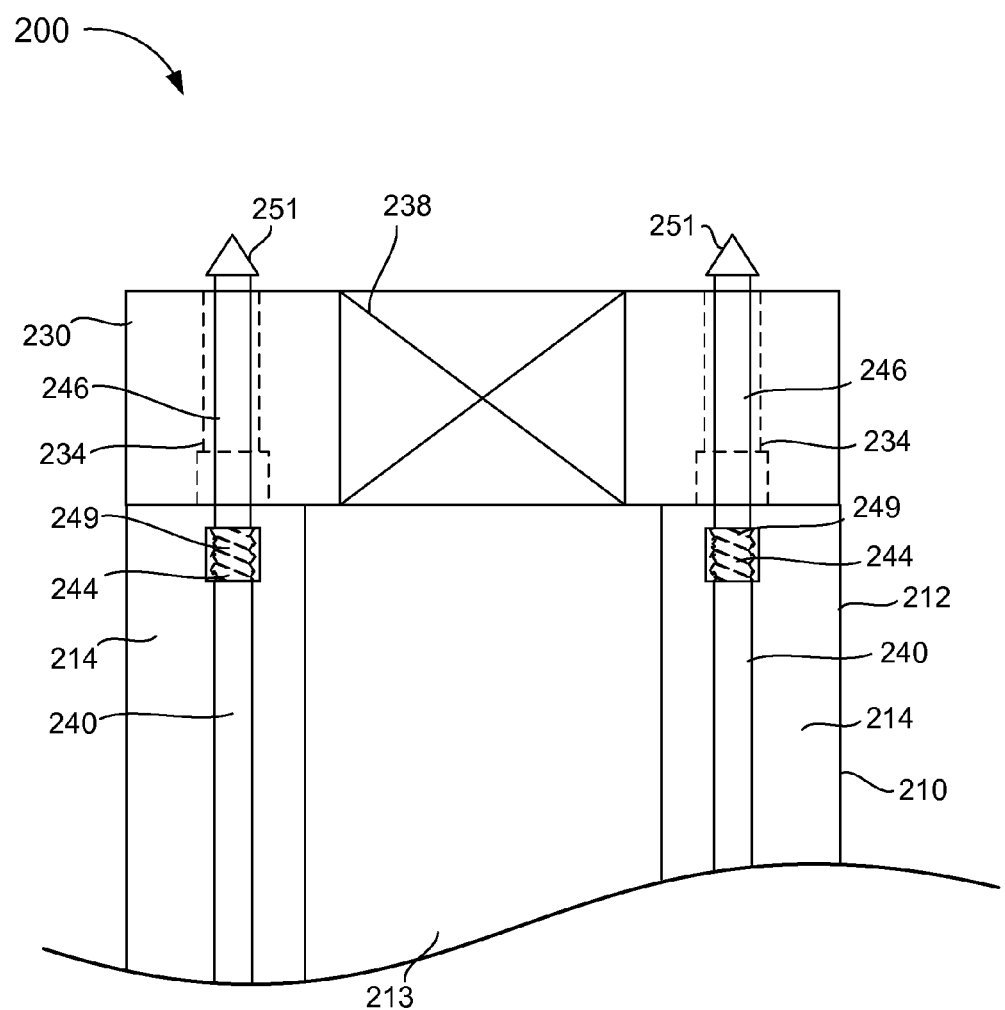
FIG. 3 is an enlarged schematic illustration of a portion of the endoleak repair device of FIG. 2.

As described above, the cannula 290 and trocar 295 can be movably disposed within the lumen 213 of the guide sheath 210. More specifically, the cannula 290 can be movably disposed within the lumen 213 of the guide sheath 210 and the trocar 295 can be movably disposed within the cannula 290. Similarly, the push rods 240 can each be movably disposed within a secondary lumen 214 defined by the guide sheath 210. For example, as shown in FIGS. 2 and 3, the guide sheath 210 can define a set of two secondary lumens 214 each of which is configured to movably receive one of the push rods 240. While shown in FIGS. 2-10 as defining two secondary lumens 214, each configured to receive one of the push rods 240, in other embodiments the guide sheath 210 can define any number of secondary lumens 214. For example, in some embodiments, the guide sheath 210 can define one, three, four, or more secondary lumens 214. Accordingly, the repair device 200 can also include any number of push rods 240 (e.g., one, three, four, or more, respectively).

The push rods 240 can be formed from any suitable material, such as, for example, stainless steel. In other embodiments, the push rods 240 can be formed from a shape memory material, such as, for example, nitinol. In still other embodiments, the push rods 240 can be formed from more than one material. For example, in some embodiments, a first portion of the push rods 240 can be formed from steel and a second portion of the push rods 240 can be formed from nitinol. The push rods 240 include a coupling portion 244 each of which is releasably coupled to a portion of the seal member 230. More specifically, as shown in FIG. 3, the repair device 200 includes a set of coupling members 246 each with a first coupling portion 249 that is releasably coupled to the coupling portion 244 of the push rods 240. Thus, the number of coupling members 246 included in the set of coupling members 246 can correspond to the number of push rods 240 included in (or housed by) the guide sheath 210. As described above, the push rods 240 can each be disposed within a different one of the secondary lumens 214 and are movable between a first position in which the coupling portion 244 (see e.g., FIG. 3) is disposed within the secondary lumen 214 and a second position in which the coupling portion 244 extends beyond the distal end portion 212 of the guide sheath 210 (see e.g., FIGS. 8 and 9), as further described herein.

The seal member 230 of the repair device 200 can be any suitable shape, size, or configuration. For example, in some embodiments, the seal member 230 can have a shape and size that corresponds to a shape and/or size of the guide sheath 210. The seal member 230 is further configured to include a hemostatic valve 238. The hemostatic valve 238 can be any suitable configuration. For example, in some embodiments, the hemostatic valve 238 can be a one-way valve that can receive at least a portion of the cannula 290 and/or the trocar 295 in a first direction while preventing passage of a flow of fluid in a second direction, opposite the first, as described in further detail herein.

The coupling members 246 each include the first coupling portion 249 (described above) and a second coupling portion 251. The coupling members 246 can be formed from any suitable material. For example, in some embodiments, the coupling members 246 can be formed from a shape memory alloy such that the coupling members 246 can be movable between a first configuration and a second configuration, as further described herein. The coupling members 246 are each movably disposed within a lumen 234 defined by the seal member 230 between a first position and a second position, relative to the seal member 230. When in the first position, the second coupling portions 251 are disposed within the lumen 234 of the seal member 230 and when the coupling members 246 are moved to their second position, the second coupling portions 251 extend outside of the lumen 234 of the seal member 230 to assume a biased configuration, as described in more detail below. More specifically, with the coupling members 246 coupled to the push rods 240, the push rods 240 can be configured to move the coupling members 246 between their first position and their second position when the push rods 240 are moved from their first position and their second position, respectively (described in further detail herein). The second coupling portion 251 of the coupling members 246 can each extend beyond a distal surface of the seal member 230 when the coupling members 246 are in the second position. As shown in FIGS. 2-4, the second coupling portions 251 can include a barbed end configured to puncture the wall of the ELG when the coupling members 246 are moved to their second position.

The coupling members 246 can be releasably coupled to the push rods 240 in any suitable manner. For example, as shown in FIG. 3, the coupling portion 244 of the push rods 240 and the first coupling portion 249 of the coupling members 246 can form a threaded coupling. In this manner, after the coupling members 246 have been moved to their second position, the push rods 240 can be rotated relative to the coupling members 246 to be decoupled from the first coupling portion 249, as further described herein.

In use, the distal end portion 212 of the guide sheath 210 can be percutaneously inserted into the common femoral artery and guided to a previously placed ELG (FIG. 4). Once at the endoleak location E (e.g., as verified with image guidance techniques such as fluoroscopy or the like), the distal end portion 212 of the guide sheath 210 can be deflected (e.g., deformed, bent, moved, or otherwise reconfigured) such that the repair device 200 is moved from its first configuration to its second configuration, as shown in FIG. 5. For example, in some embodiments, a user can manipulate a mechanism (not shown in FIGS. 2-10) included in a handle 260 (not shown in FIGS. 2-10) of the repair device 200 that can be used to actuate the guide sheath 210 to deflect the distal end portion 212 of the guide sheath 210. In some embodiments, the mechanism can be a button, a slider, a dial, a twist or spiral drive, or the like that is at least operably coupled to the distal end portion 212. In other embodiments, the mechanism can be a toggle included in an electronic circuit. For example, in some embodiments, the toggle can be moved to complete an electronic circuit that can in turn allow an electrochemical actuator to discharge. In such embodiments, the electrochemical actuator can be configured to deform during discharge and thus can deflect the guide sheath 210.

Figure 6:
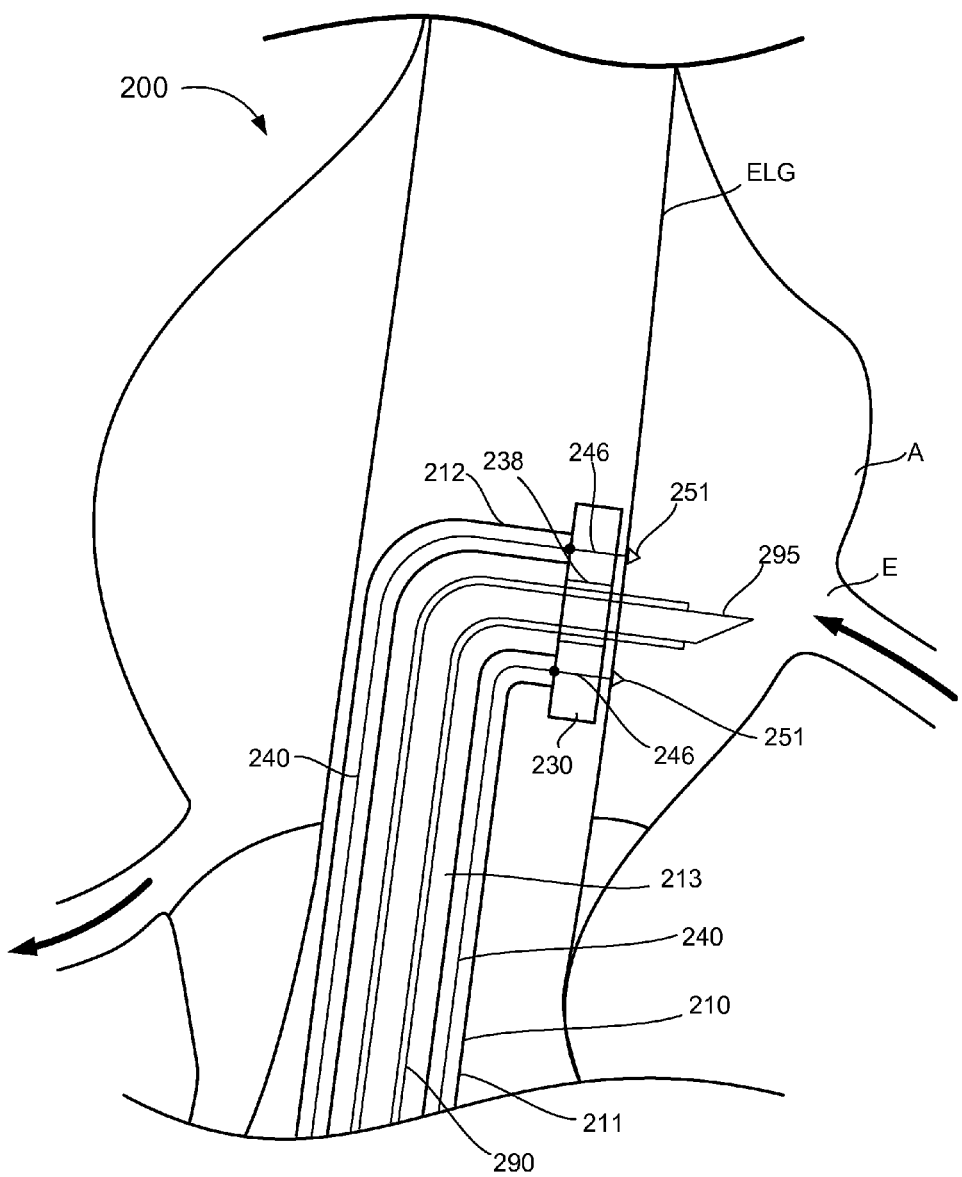
FIG. 6 is a schematic illustration of the endoleak repair device of FIG. 2 in use within the endoluminal graft, in a third configuration.

The guide sheath 210 can be placed in its second configuration such that the distal end portion 212 is moved to an angled or curved orientation relative to a longitudinal axis of the guide sheath 210. For example, as shown in FIGS. 5-7 the distal end portion 212 of the guide sheath 210 can be substantially perpendicular to the wall of the ELG. Moreover, the distal end portion 212 can be placed adjacent to the wall of the ELG such that the seal member 230 is placed in contact with (or adjacent to) the wall of the ELG. In this manner, the second coupling portion 251 of the coupling member 246 can be moved in a distal direction such that the barbed end of the second coupling portion 251 punctures the wall of the ELG to temporarily couple the guide sheath 210 thereto, as shown, for example, in FIGS. 5 and 6.

With the seal member 230 at least temporarily coupled to the ELG wall, the cannula 290 and trocar 295 can be moved or advanced towards the distal end portion 212 of the guide sheath 210 (if not already disposed at the distal end portion 212 of the guide sheath 210). The cannula 290 and/or the trocar 295 can be advanced through the hemostatic valve 238 included in the seal member 230 (thereby placing the valve 238 in the open configuration) to allow the trocar 295 to puncture the wall of the ELG. In this manner, a portion of the cannula 290 and/or trocar 295 can be disposed within the aneurysm sac A (FIG. 6). The trocar 295 can then be retracted toward the proximal end portion 211 of the endoleak repair device 200. With the trocar 295 retracted, the cannula 290 can be used to deliver any suitable embolic treatment to the leak site (e.g., a sealing agent). For example, coils, glues, thrombin, fibrin, procoagulants, onyx, and/or any other suitable material can be delivered to the endoleak site. In some embodiments, the delivered material fills the area of the sac previously filled by pooling blood and at least a portion of the lumbar and/or inferior mesenteric arteries can be embolized, thus, sealing the endoleak. In some embodiments, the embolic agent can be delivered without retracting the trocar 295.

As shown in FIGS. 7 and 8, after the treatment is delivered, the cannula 290 can be retracted and the repair device 200 can be moved to the fourth configuration. To move the repair device 200 to the fourth configuration, the push rods 240 can be advanced in a distal direction to their second position and thus move the coupling members 246 distally to their second position. As shown in FIG. 8, the movement of the coupling members 246 to their second position can be such that the second coupling portions 251 are advanced in a distal direction relative to the seal member 230. Furthermore, with the coupling members 246 formed (at least in part) from a shape memory alloy, the second coupling portion 251 can move to their second configuration in which the second coupling portion 251 coils, bends, and/or otherwise reconfigures (FIG. 8). Thus, when in the second configuration, the second coupling portion 251 of the coupling members 246 each maintain the seal member 230 in contact with the wall of the ELG. Expanding further, the first coupling portion 249 is moved distally into contact with a proximal surface of the seal member 230 when the coupling member 246 is moved to its second position. In this manner, the second coupling portion 251 (when in the second configuration) and the first coupling portion 249 can collectively exert a compressive force on the seal member 230 and the wall of the ELG. Thus, the seal member 230 can form a fluidic seal with the wall of the ELG.

With the seal member 230 coupled to the ELG wall and with the cannula 290 and trocar 295 retracted, the hemostatic valve 238 can prevent a flow of a fluid through the valve 238, thus the seal member 230 seals the hole formed by the trocar 295 puncturing the ELG wall. In this manner, the ELG and the endoleak location E are sealed and the guide sheath 210 can be decoupled from the seal member 230 thereby placing the repair device 200 in the fifth configuration (FIGS. 9 and 10). For example, the push rods 240 can be rotated relative to the coupling member 246 to decouple the threaded coupling therebetween (e.g., between the coupling portion 244 and the first coupling portion 249 of the coupling member 246). In this manner, the guide sheath 210 can be decoupled from the seal member 230. Once decoupled, the guide sheath 210 can be retracted through the common femoral artery and the seal member 230 can remain coupled to the ELG wall, thereby sealing the endoleak (FIG. 10).

While the second coupling portion 251 of the coupling member 246 is particularly described above in FIGS. 2-10, in other embodiments, the second coupling portion 251 can be any suitable configuration. For example, in some embodiments, a coupling member can include a second coupling portion that includes J-hooks or the like. In other embodiments, a seal member can be at least temporarily held in place by a clamp, forceps, suture or the like.

Figure 11:
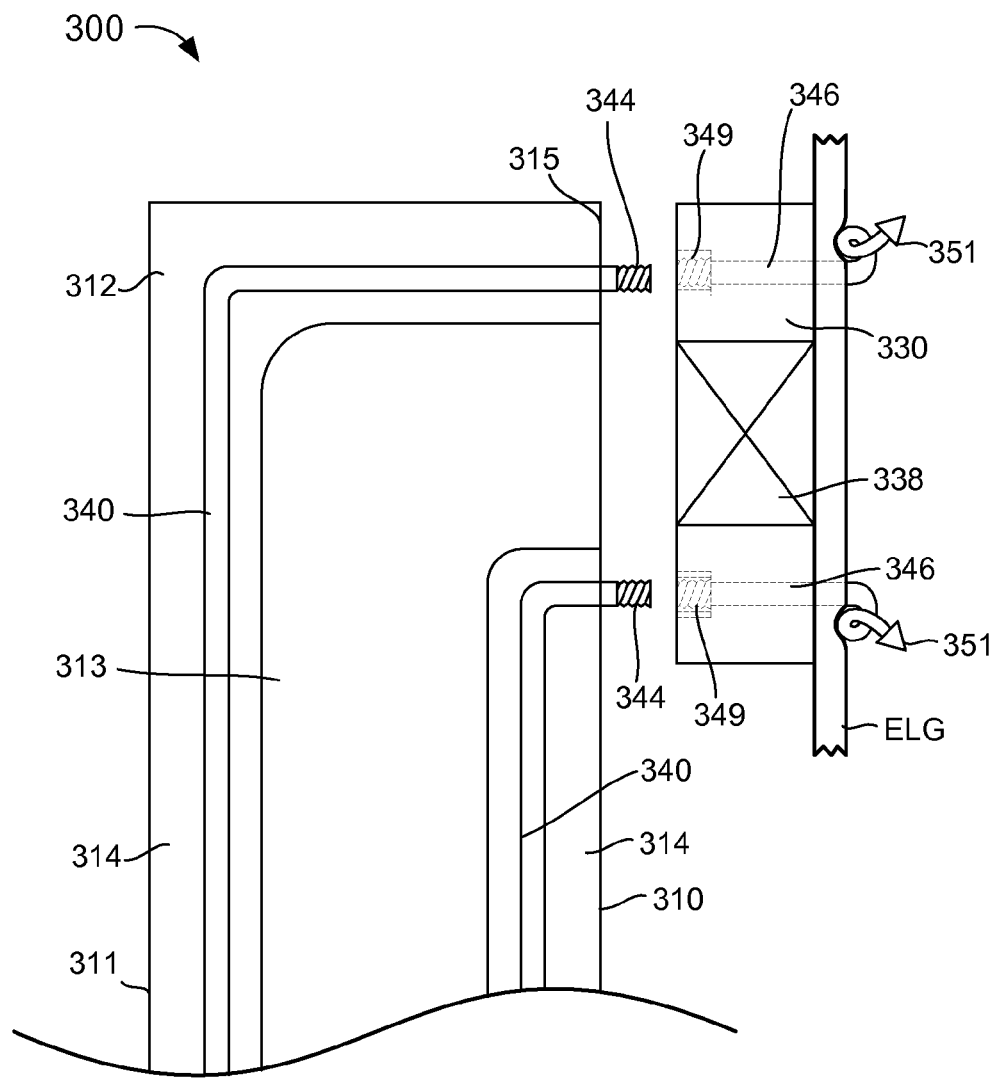
FIG. 11 is a schematic illustration of an endoleak repair device, according to an embodiment.
Figure 12:
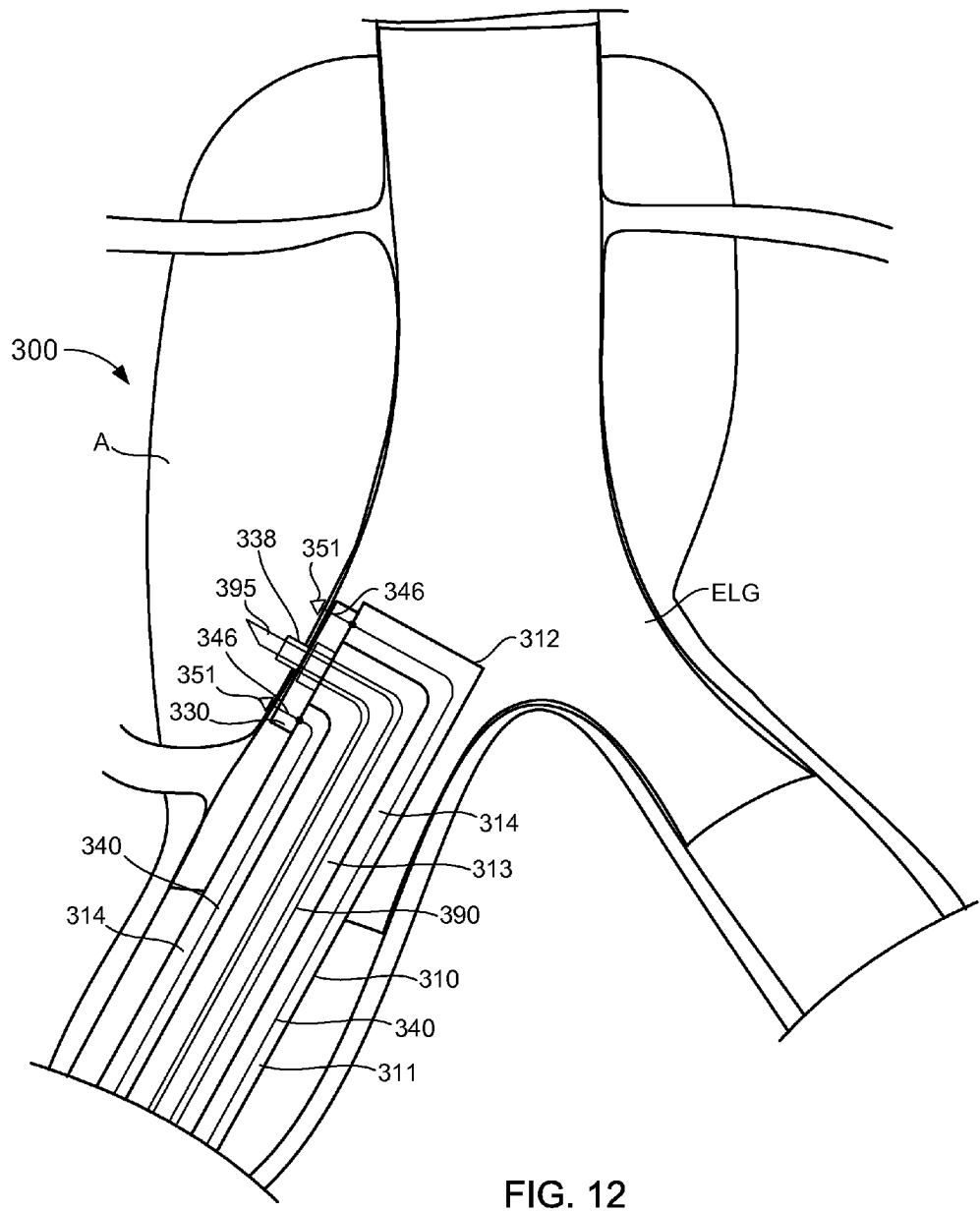
FIG. 12 is a schematic illustration of the endoleak repair device of FIG. 11 in use within an endoluminal graft.

While the seal member 230 is shown in FIGS. 2-10 as extending from a distal end of the guide sheath 210, in some embodiments, a seal member can be removably coupled to a side of the guide sheath. For example, FIGS. 11 and 12 illustrate an endoleak repair device 300 according to another embodiment. In some embodiments, various aspects of the endoleak repair device 300 can be similar in form and function to corresponding aspects of the endoleak repair device 200, described above with reference to FIGS. 2-10. Therefore, certain aspects of the endoleak repair device 300 are not described in further detail herein.

As shown in FIG. 11, the endoleak repair device 300 includes a guide sheath 310, a seal member 330, a set of push rods 340, a cannula 390, and a trocar 395. The guide sheath 310 includes a proximal end portion 311 and a distal end portion 312 and defines a lumen 313 and a set of secondary lumens 314 therebetween. The lumen 313 of the guide sheath 310 can receive at least a portion of the cannula 390. The secondary lumens 314 are each configured to receive at least a portion of one of the push rods 340. More specifically, the cannula 390 (and the trocar 395) is movably disposed within the lumen 313, and the push rods 340 are each movably disposed within a different one of the secondary lumens 314.

As shown in FIGS. 11 and 12, the seal member 330 can be releasably coupled to a side wall 315 of the guide sheath 310 such that the distal end portion 312 need not be deflected to place the guide sheath 310 and/or the seal member 330 in a desired position relative to an ELG. In other embodiments, the distal end portion 312 of the guide sheath 310 can be configured to bend, twist, deform, or otherwise reconfigure between a first configuration and a second configuration, as described in detail with respect to FIGS. 2-10.

The seal member 330 includes a hemostatic valve 338 that can receive a portion of the cannula 190 and/or trocar 195. For example, as described in detail above with reference to FIGS. 2-10, the cannula 390 and/or trocar 395 can be inserted through the hemostatic valve 338 of the seal member 330 such that the trocar 395 can puncture the wall of the ELG. In this manner, at least a portion of the cannula 390 and/or the trocar 395 can be inserted into an aneurysm sac. In some embodiments, the trocar 395 can be retracted and a sealing agent can be delivered through the cannula 390 and into the aneurysm sac.

The repair device 300 includes a set of coupling members 346. The coupling members 346 include a first coupling portion 349 and a second coupling portion 351. The first coupling portion 349 is configured to be releasably coupled to a coupling portion 344 of the push rods 340, as described above. In this manner, the first coupling portion 349 releasably couples the seal member 330 to the guide sheath 310. The second coupling portion 351 is configured to be advanced through the ELG wall to couple the seal member 330 thereto, as described above with reference to FIGS. 2-10. As shown in FIG. 11, the push rods 340 are configured to extend from the sidewall 315 of the guide sheath 310 such that the seal member 330 is releasably coupled to the sidewall 315.

In use, for example, as shown in FIG. 12, the endoleak repair device 300 can be inserted into an endoluminal graft (ELG) to embolize, for example, a type 2 endoleak. More specifically, with the seal member 330 releasably coupled to the side wall 315 of the guide sheath 310, the endoleak repair device 300 can be used to repair an endoleak located in, for example, an iliac branch of the aorta. Similarly stated, with the seal member 330 releasably coupled to the side wall 315 of the guide sheath 310, the size of the endoleak repair device 300 can be sufficiently small such that the endoleak repair device 300 can be maneuvered within the iliac branch to repair a type 2 endoleak into an aneurysm sac A. In this manner, the endoleak repair device 300 can be positioned at a desired location and can embolize the type 2 endoleak in a similar manner to the endoleak repair device 200 described above with reference to FIGS. 2-10. However, with the seal member 330 releasably coupled to the side wall 315 of the guide sheath 310, the deflection of the distal end portion 312 (e.g., such as to place the seal member 330 in the desired location relative to the wall of the ELG and/or the endoleak) may be reduced or negated, thereby allowing for the embolization of an endoleak located at or near the iliac branch of the aorta.

Figure 20:
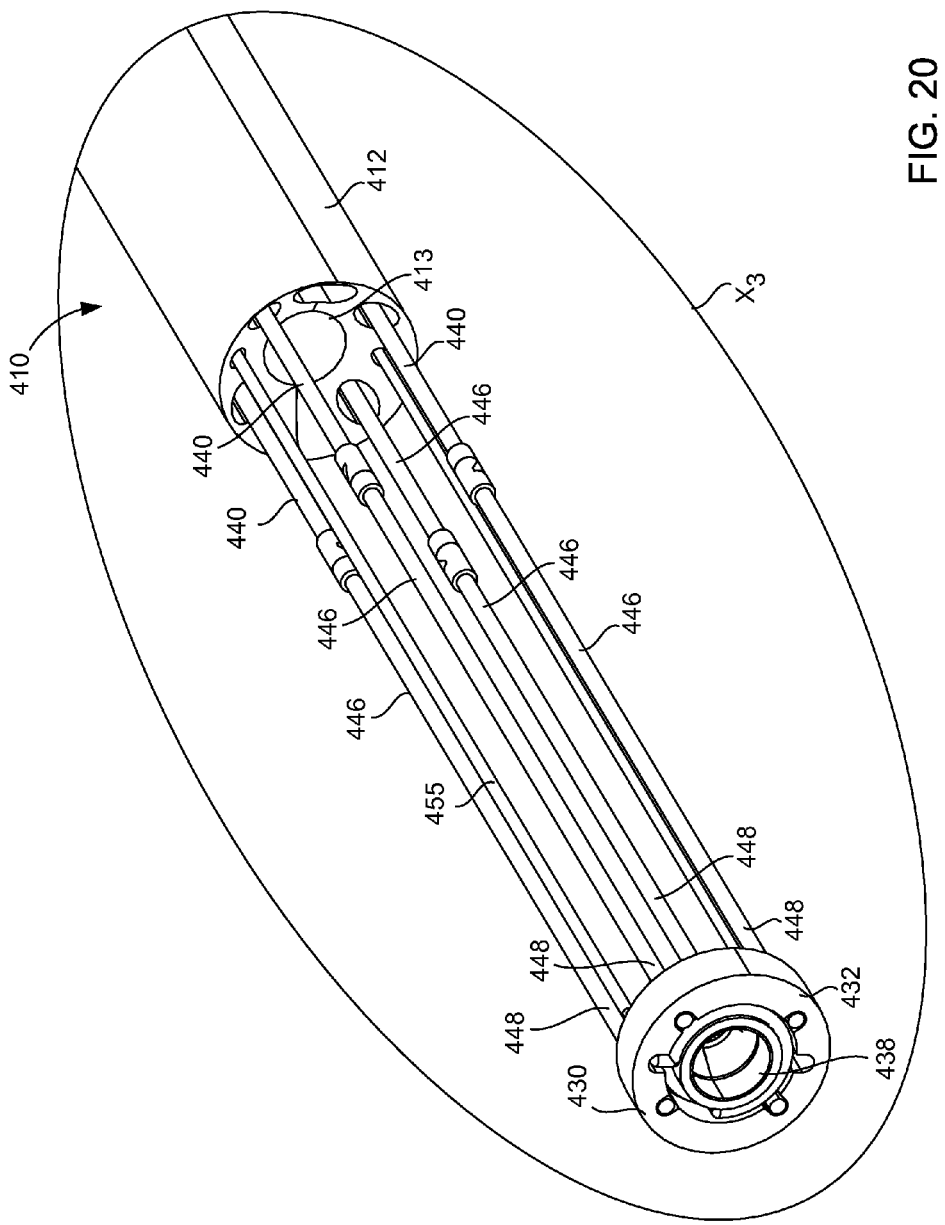
FIG. 20 is an enlarged perspective view of a portion of the endoleak repair device of FIG. 13, identified as region $X_3$ in FIG. 19.
Figure 21:
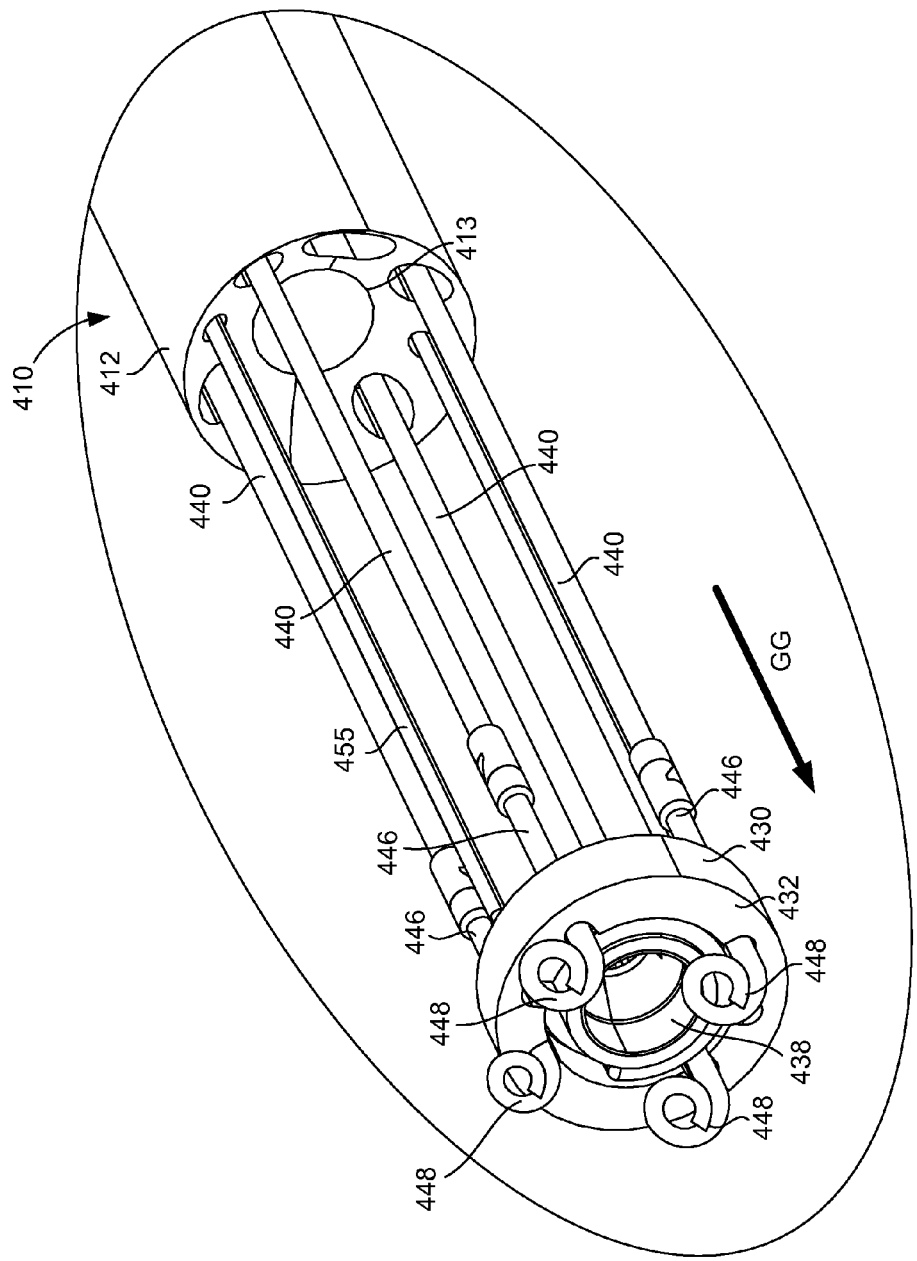
FIG. 21 is an enlarged perspective view of the portion of the endoleak repair device of FIG. 20, in the third configuration.
Figure 22:
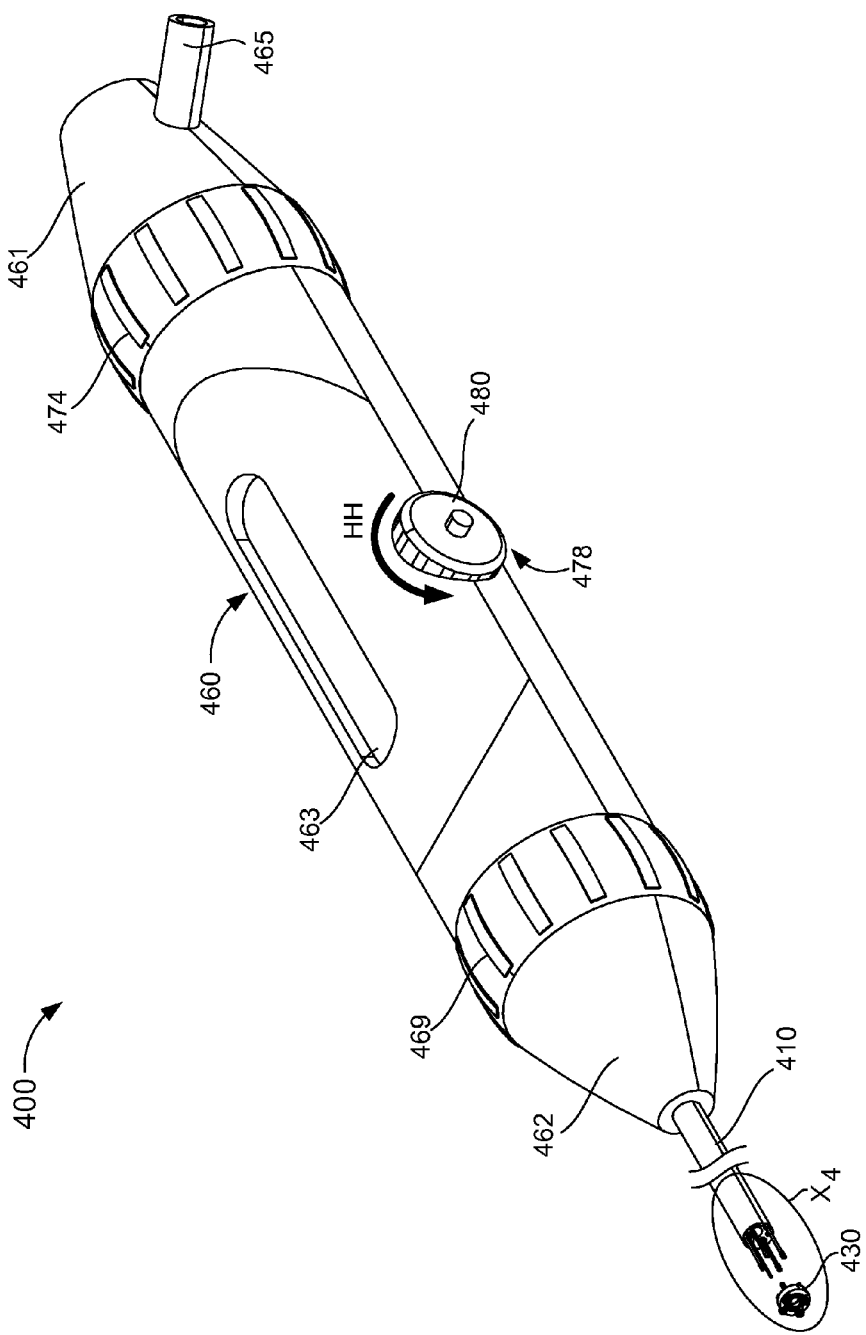
FIG. 22 is a perspective view of the endoleak repair device of FIG. 13, in a fourth configuration.
Figure 23:
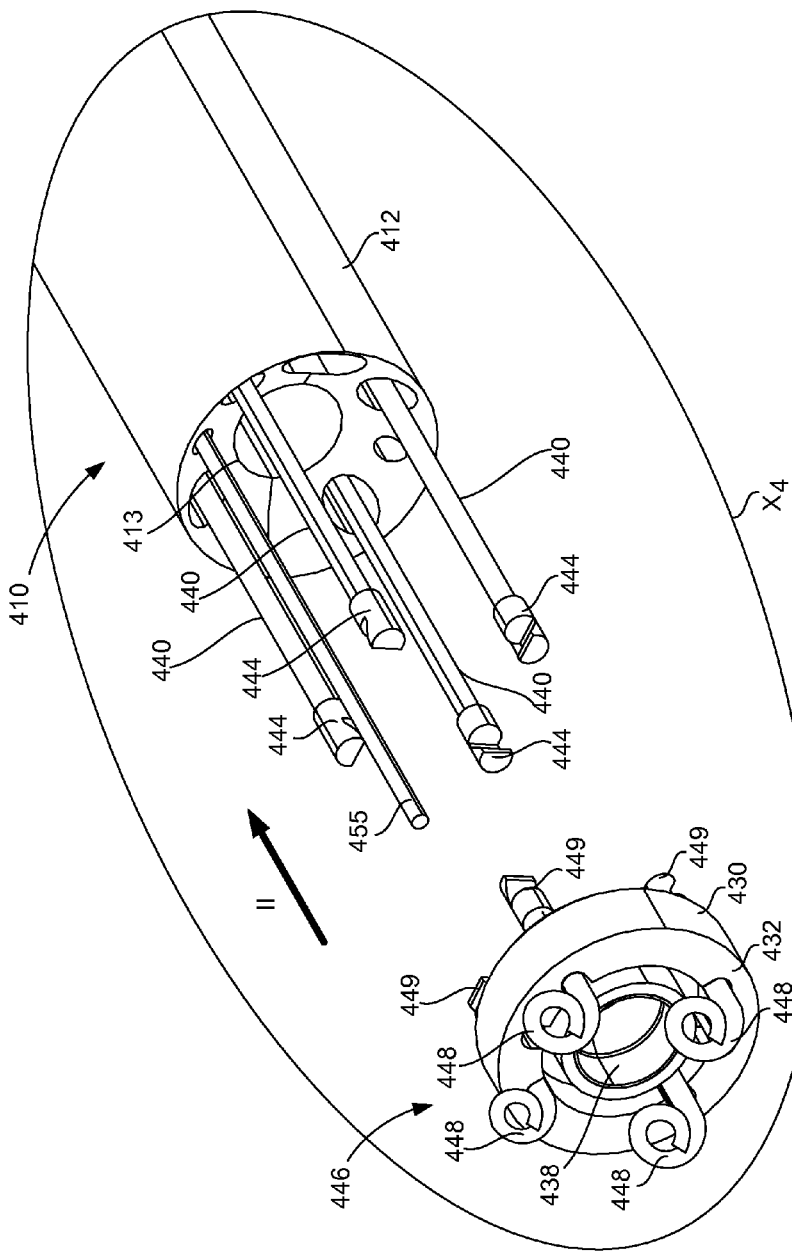
FIG. 23 is an enlarged perspective view of a portion of the endoleak repair device of FIG. 13, identified as region $X_4$ in FIG. 22.

Referring now to FIGS. 13-23, various views of an endoleak repair device 400 are shown, according to an embodiment. The endoleak repair device 400 (also referred to herein as "repair device") includes a deformable guide sheath 410 (also referred to herein as "guide sheath 410"), a detachable seal member 430, a set of push rods 440, a retention member 455, a deflection member 456, and a handle 460. As described in further detail herein, the repair device 400 is configured to be moved between a first configuration (FIG. 13), a second configuration (FIG. 18), a third configuration (FIGS. 19-21), and a fourth configuration (FIGS. 22 and 23).

Figure 13:
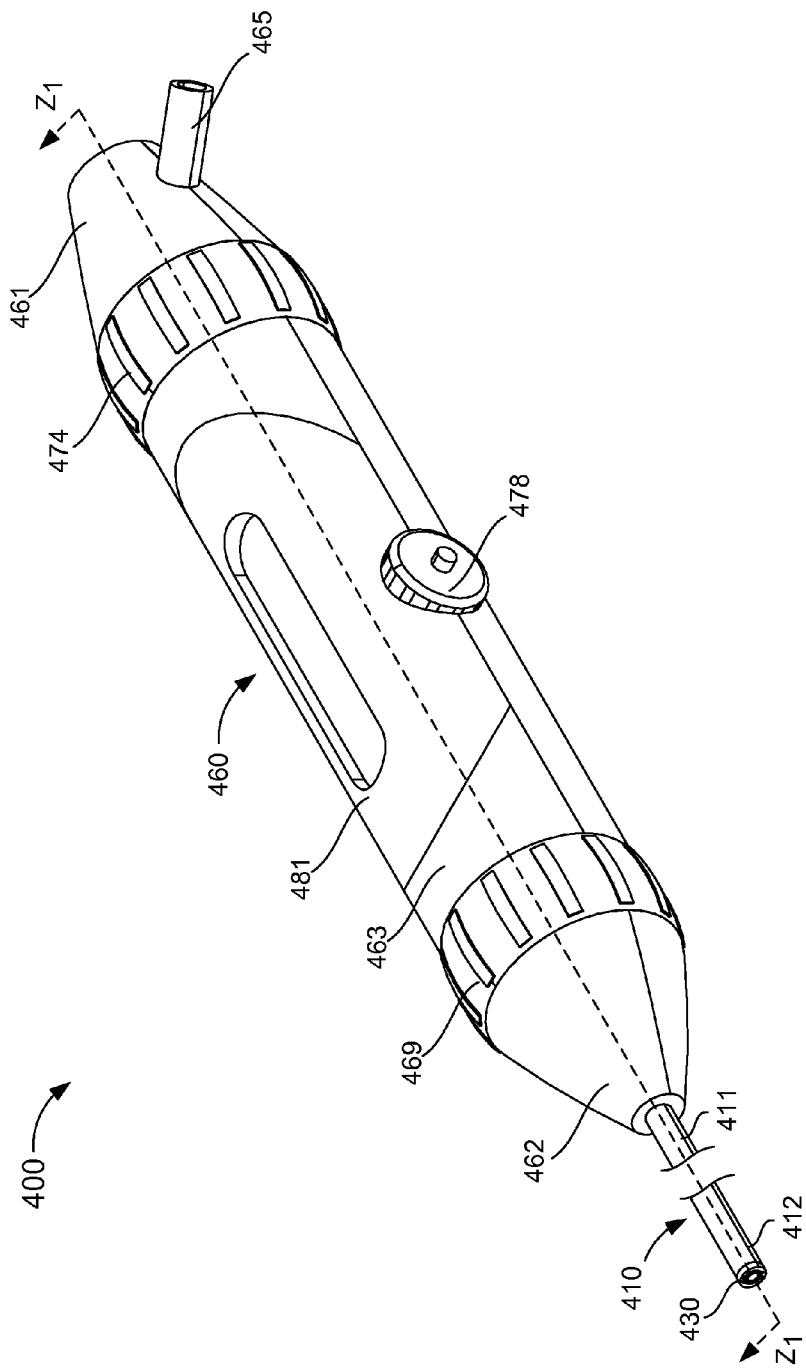
FIG. 13 is a perspective view of an endoleak repair device in a first configuration, according to another embodiment.

As shown in FIG. 13, the handle 460 of the repair device 400 includes a proximal end portion 461, a distal end portion 462, a body portion 463, a set of alignment rods 473, and a retention mechanism 478 (see e.g., FIG. 21). As shown, for example, in FIGS. 13 and 14, the body portion 463 can be coupled to a body cover 481 (e.g., via a press fit, a friction fit, an adhesive, one or more tabs, or any other suitable coupling method). In this manner, the body portion 463 and the body cover 481 define an inner volume 464 that can house or be coupled to at least a portion of the guide sheath 410, the push rods 440, the retention member 455, the deflection member 456, the alignment rods 473, and the retention mechanism 478 (see e.g., FIG. 14).

Figure 14:
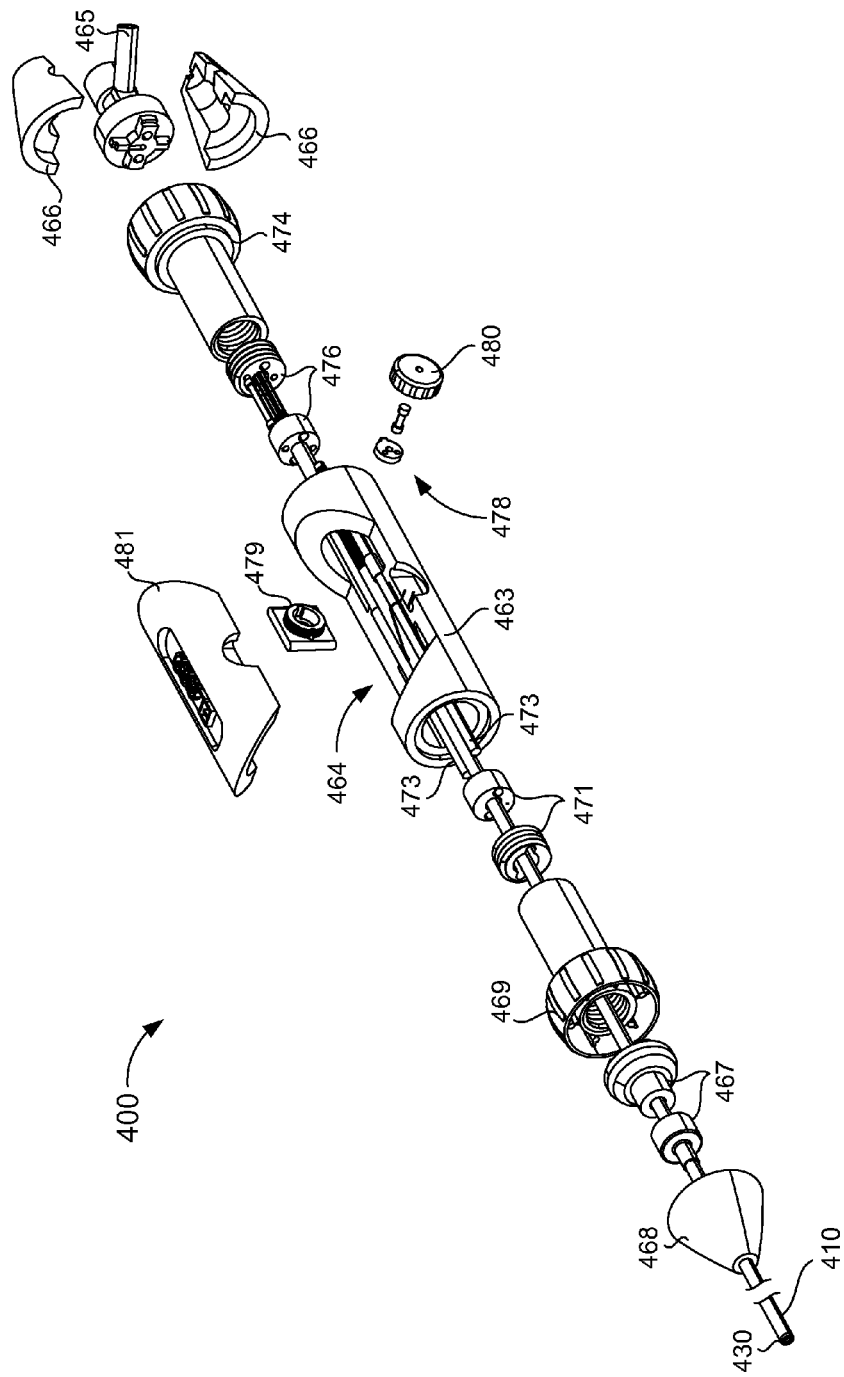
FIG. 14 is an exploded perspective view of the endoleak repair device of FIG. 13.

The retention mechanism 478 includes at least a threaded base 479 and a threaded cap 480 (each shown, for example, in FIG. 14). The retention member 455 can be selectively coupled to the threaded base 479 and or the threaded cap 480. More specifically, the threaded cap 480 can be disposed about the threaded base 479 to retain the retention member 455 in a fixed position relative to the handle 460. The threaded cap 480 can be decoupled (e.g., advanced along the threads) from the threaded base 479 to allow access to a proximal end portion of the retention member 455, as further described herein.

Figure 18:
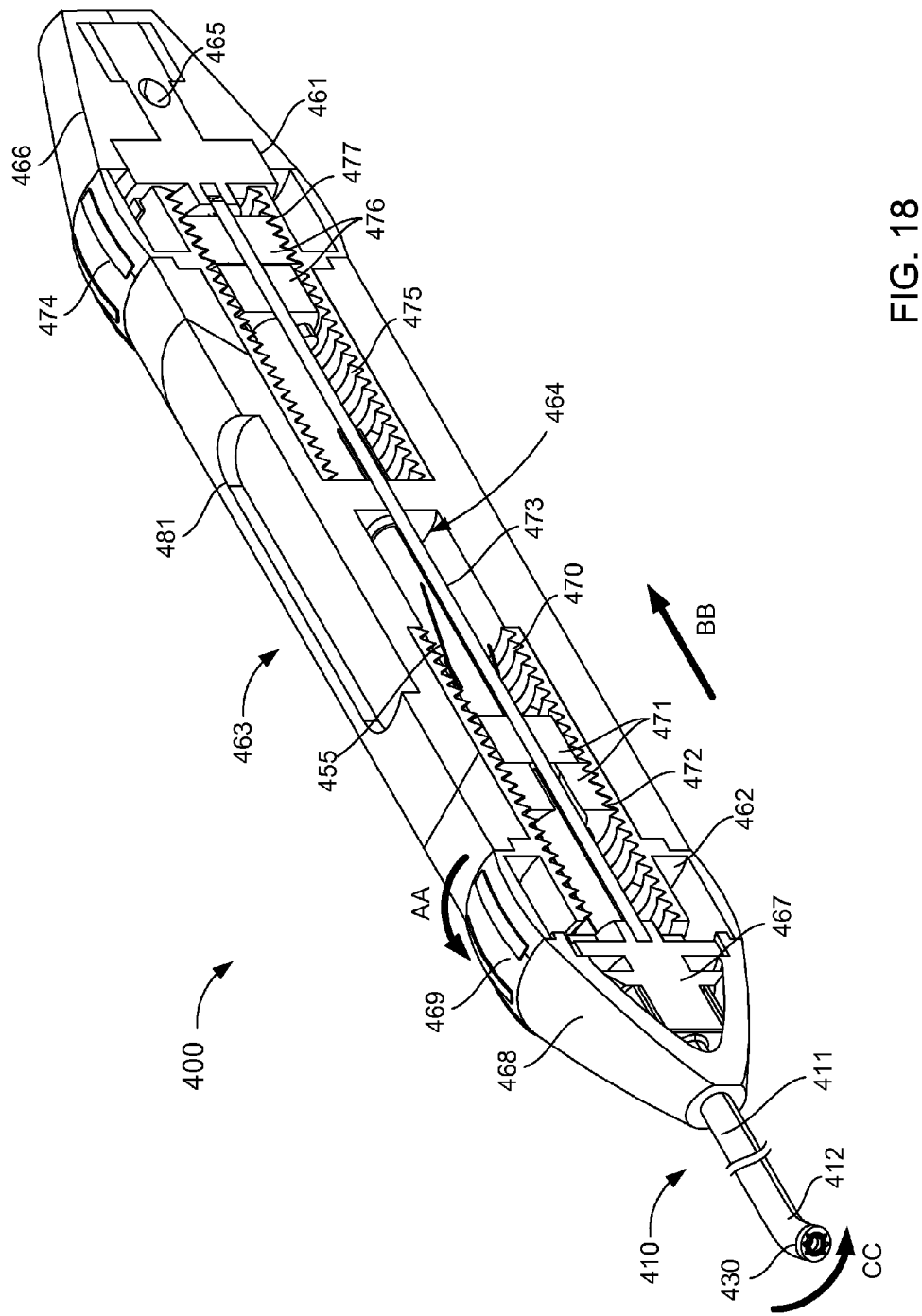
FIG. 18 is a cross-sectional view of the endoleak repair device taken along the line $Z_1$-$Z_1$ in FIG. 13, in a second configuration.
Figure 19:
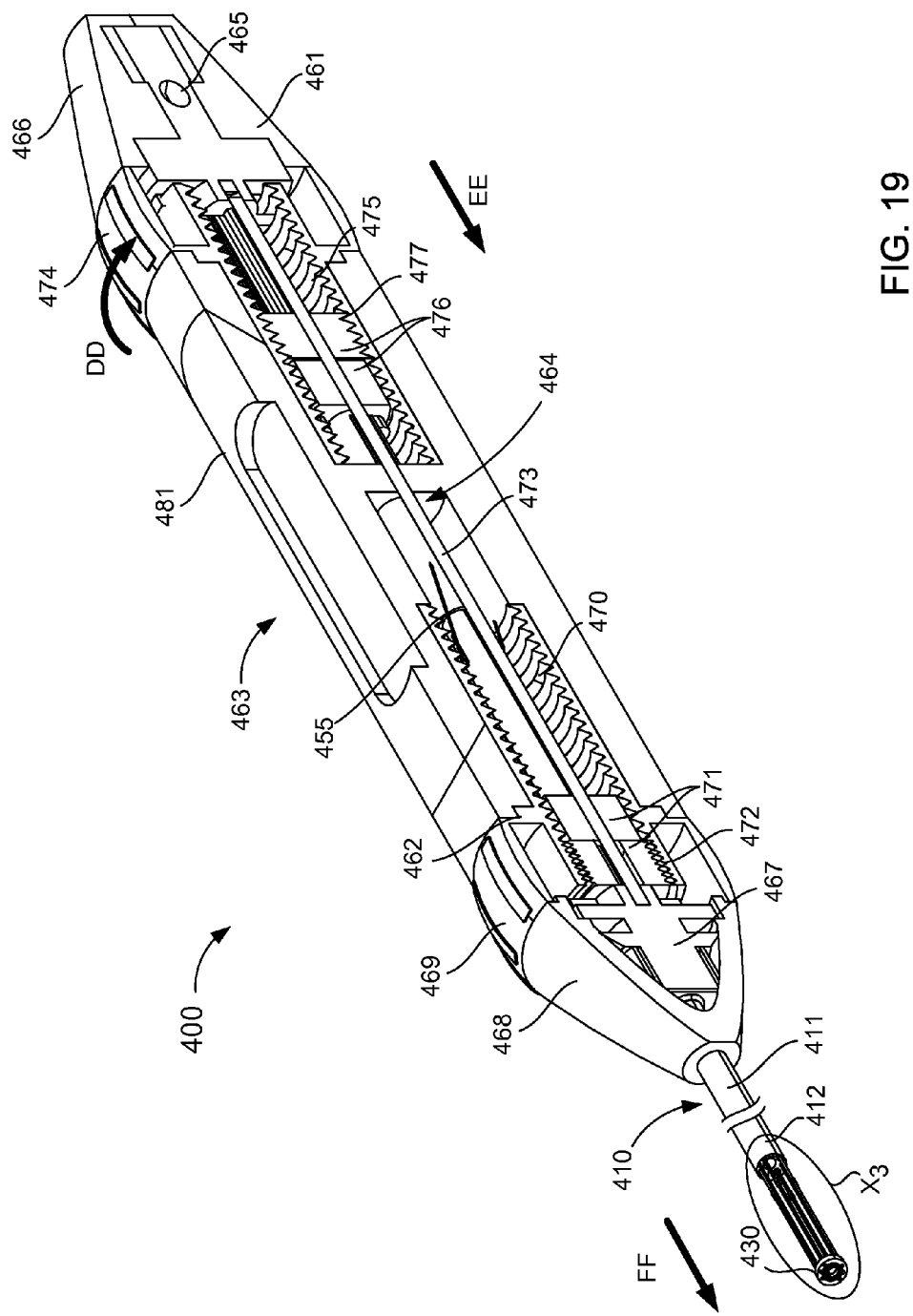
FIG. 19 is a cross-sectional view of the endoleak repair device taken along the line $Z_1$-$Z_1$ in FIG. 13, in a third configuration.

As shown, for example, in FIGS. 14, 18 and 19, the proximal end portion 461 of the handle 460 includes a port 465, a proximal cover 466, a proximal rotation member 474, and a proximal shuttle 476. As shown, for example, in FIG. 14, the proximal cover 466 is configured to enclose at least a portion of the proximal port 465. The proximal port 465 is in communication with a portion of the guide sheath 410. More specifically, the proximal port 465 can be configured to receive a cannula (with or without a trocar) such that the cannula can be disposed within a lumen 413 (see, e.g., FIGS. 15, 20, 21 and 23) defined by the guide sheath 410, as further described herein.

The proximal rotation member 474 of the handle 460 is configured to be partially disposed within the inner volume 464 of the body portion 463 such that the proximal rotation member 474 can be rotated relative to the body portion 463. In a similar manner, the proximal shuttle 476 is disposed within a portion of the proximal rotation member 474 and is configured to move along the alignment rods 473, relative to the proximal rotation member 475, as shown for example, in FIGS. 18 and 19. For example, the proximal rotation member 474 includes a threaded inner surface 475 that engages a threaded outer surface 477 of the shuttle 476 such that when the proximal rotation member 474 is rotated, the proximal shuttle 476 is advanced along the threaded surface 475 of the proximal rotation member 474. Moreover, the proximal shuttle 476 can be coupled to a proximal end portion of the push rods 440 such that when the proximal shuttle 476 is advanced along the threaded surface 475, the proximal shuttle 476 moves the push rods 440 relative to the guide sheath 410, as further described herein.

The distal end portion 462 of the handle 460 includes a distal alignment member 467, a distal cover 468, a distal rotation member 469, and a distal shuttle 471, as shown in FIGS. 14, 18 and 19. The distal cover 468 is configured to enclose at least a portion of the distal alignment member 467. The distal alignment member 467 is also configured to be at least partially disposed within a portion of the distal rotation member 469. Moreover, the distal alignment member 467 defines an aperture that can receive the guide sheath 410. Thus, with the distal alignment member 467 at least partially disposed within the distal rotation member 469, the distal alignment member 467 can limit a movement of a portion of the guide sheath 410 relative to the distal rotation member 469.

The distal rotation member 469 of the handle 460 is configured to be partially disposed within the inner volume 464 of the body portion 463 such that the distal rotation member 469 can be rotated relative to the body portion 463. In a similar manner, the distal shuttle 471 is disposed within a portion of the distal rotation member 469 and is configured to move along the alignment rods 473, relative to the distal rotation member 469. For example, as shown in FIGS. 18 and 19, the distal rotation member 469 includes a threaded inner surface 470 that engages a threaded outer surface 472 of the shuttle 471 such that when the distal rotation member 469 is rotated, the distal shuttle 471 is advanced along the threaded surface 470 of the proximal rotation member 469. Moreover, the distal shuttle 471 can be coupled to a proximal end portion of the deflection member 456 such that when the distal shuttle 471 is advanced along the threaded surface 470, the distal shuttle 471 moves the deflection member 456 relative to the guide sheath 410, as further described herein.

The guide sheath 410 includes a proximal end portion 411 and a distal end portion 412 and defines the lumen 413 and a set of secondary lumen 414 therebetween. The guide sheath 410 can be any suitable shape, size, or configuration. For example, in some embodiments, the guide sheath 410 can be a cylindrical elongate member. Moreover, the length and/or diameter of the guide sheath 410 can correspond with the size and/or configuration of an endoluminal graft (ELG) into which the guide sheath 410 is inserted. For example, in some embodiments, the guide sheath 410 can be sufficiently long to be inserted through a common femoral artery and guided into a desired position within an ELG disposed within an aorta of a patient.

As described in further detail herein, the distal end portion 412 of the guide sheath 410 is releasably coupled to the seal member 430 and is configured to move (e.g., bend, deflect, deform, or otherwise reconfigure) between a first configuration (see e.g., FIG. 13) and a second configuration (see e.g., FIG. 18). The proximal end portion 411 of the guide sheath 410 is coupled to and/or otherwise disposed within the handle 460 (see e.g., FIG. 14). As described above, the proximal end portion 411 can be arranged relative to the handle 460 such that a cannula and trocar (not shown in FIGS. 13-23) can be inserted into the proximal port 465 of the handle 460 and into the lumen 413 defined by the guide sheath 410. Similarly stated, the cannula and trocar can be movably disposed within the lumen 413 defined by the guide sheath 410, as described in further detail herein.

Figure 15:
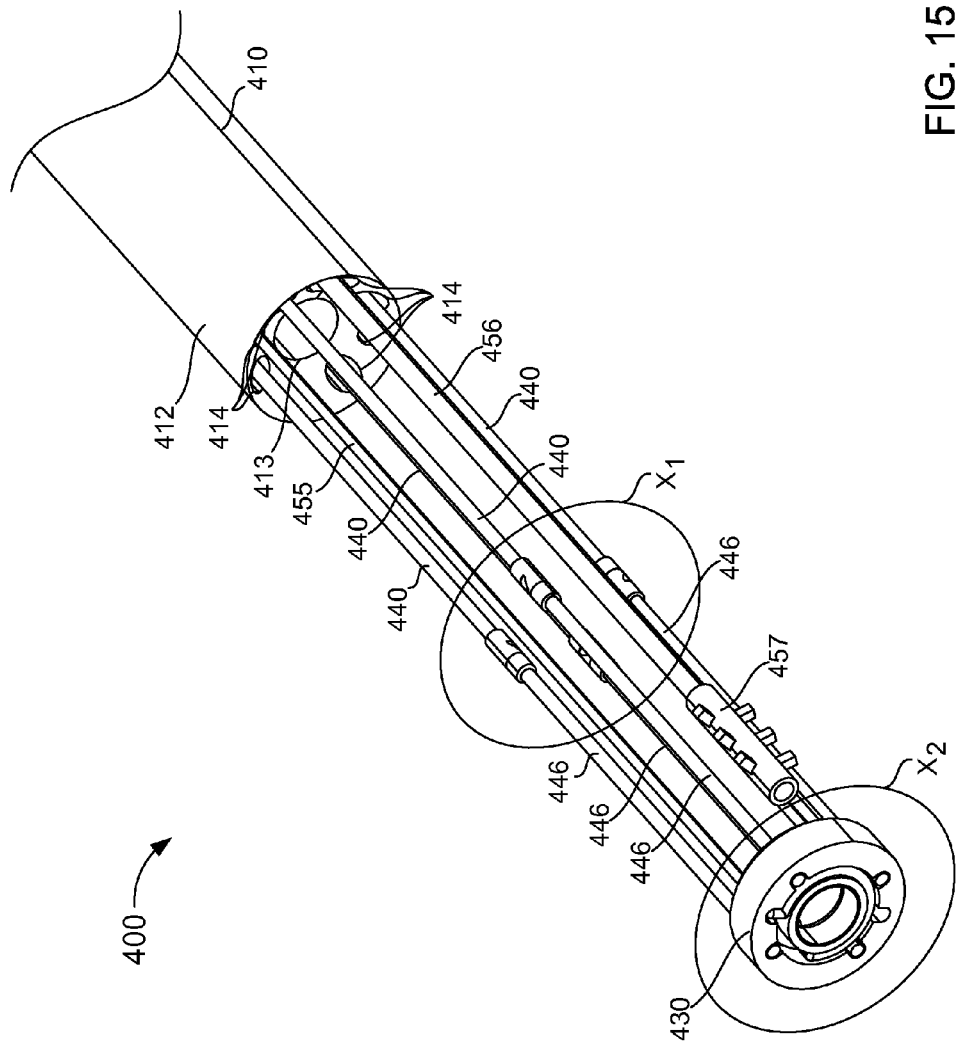
FIG. 15 is a perspective view of a portion of the endoleak repair device of FIG. 13.

The secondary lumen 414 defined by the guide sheath 410 can house at least a portion of the push rods 440, the retention member 455, and the deflection member 456 (see e.g., FIG. 15). Expanding further, the push rods 440, the retention member 455, and the deflection member 456 can each be movably disposed within a different one of the secondary lumen 414. While shown in FIG. 15 as including multiple secondary lumen 414 each of which housing one of the push rods 440, the retention member 455 or the deflection member 456, in other embodiments, the guide sheath 410 can define any suitable number of secondary lumen 414 that can be in any suitable configuration. For example, in some embodiments, a guide sheath can include one secondary lumen configured to house the push rods 440, the retention member 455, and the deflection member 456. In other embodiments, the lumen 413 and the secondary lumen 414 can be combined. Similarly stated, in some embodiments, a guide sheath can have a substantially annular shape and can define a single lumen that can receive a cannula (with or without a trocar), the push rods 440, the retention member 455, and the deflection member 456.

The deflection member 456 of the repair device 400 is movably disposed within one of the secondary lumen 414 defined by the guide sheath 410. Expanding further, the deflection member 456 includes the proximal end portion that is coupled to the distal shuttle 471 of the handle 460 and a distal end portion that is coupled to an engagement member 457 (see the exploded view of FIG. 15). The engagement member 457 is configured to be fixedly disposed within the secondary lumen 414 of the guide sheath 410 along with the deflection member 456 and fixedly coupled to the distal end portion of the deflection member 456. In this manner, a user can manipulate the handle 460 (e.g., rotate the distal rotation member 469) to move of the deflection member 456, which in turn deflects the distal end portion 412 of the guide sheath 410, as further described herein.

The push rods 440 of the repair device 440 are each movably disposed within a different secondary lumen 414 defined by the guide sheath 410. The push rods 440 can be formed from any suitable material, such as, for example, stainless steel. In other embodiments, the push rods 440 can be formed from a shape memory material, such as, for example, nitinol. In some embodiments, the push rods 440 can be formed from more than one material. For example, a first portion of the push rods 440 can be formed from, for example, stainless steel and a second portion of the push rods 440 can be formed from, for example, nitinol. In this manner, the first portion can have a stiffness that is greater than a stiffness of the second portion. Each of the push rods 440 can be coupled to a coupling member 446. The coupling members 446 can be formed from, for example, a shape memory material such as nitinol, and can be moved between a first configuration (associated with a first shape) and a second configuration (associated with a second shape), as further described herein.

Figure 16:
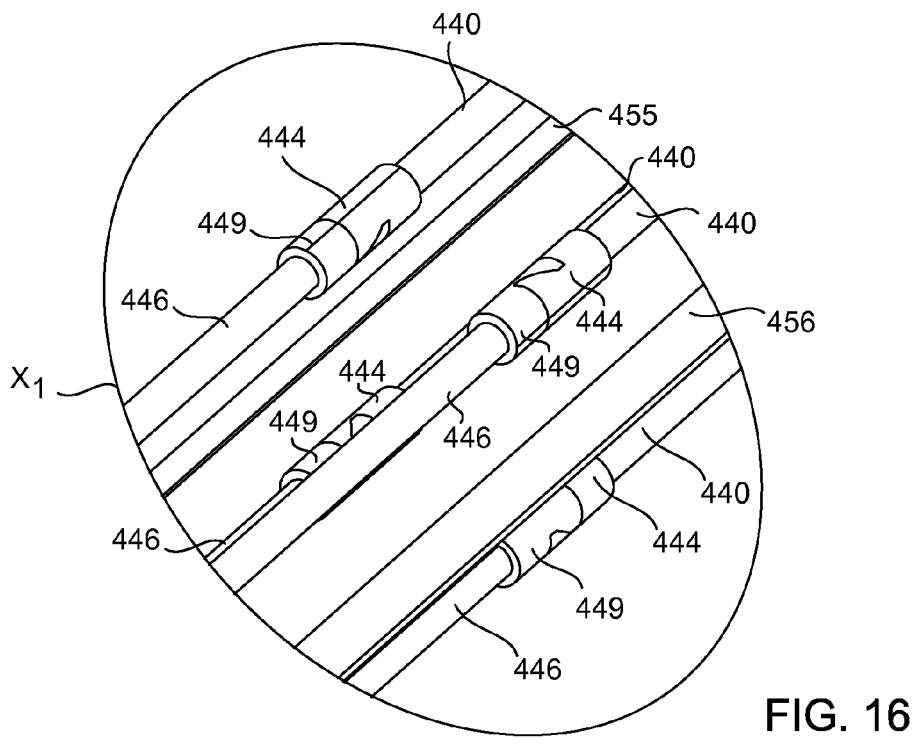
FIG. 16 is an enlarged perspective view of a portion of the endoleak repair device of FIG. 13, identified as region $X_1$ in FIG. 15.

The push rods 440 include a coupling member or portion 444 disposed at a distal end portion that is configured to be releasably coupled to a coupling portion 449 (also referred to as "first coupling portion") disposed at a proximal end portion of the coupling member 446. For example, as shown in FIG. 16, the coupling portion 444 of the push rods 440 and the coupling portion 449 of the coupling members 446 each have a shape defining a latch such that the coupling portions 444 and 449 can be, at least temporarily, matingly coupled to each other. In this manner, when the push rods 440 and the coupling members 446 are coupled together, the push rods 440 and the coupling members 446 can be collectively moved relative to the guide sheath 410. For example, as described above, the push rods 440 each include the proximal end portion that is coupled to the proximal shuttle 471 of the handle 460. Thus, a user can manipulate the handle 460 (e.g., rotate the proximal rotation member 469) to move the push rods 440 relative to the guide sheath 410, as further described herein.

The seal member 430 of the repair device 400 is at least temporarily coupled to the distal end portion 412 of the guide sheath 410 (see e.g., FIG. 13). The seal member 430 can be any suitable shape, size, or configuration. For example, in some embodiments, the seal member 430 can have a shape and size that corresponds to the guide sheath 410 (e.g., the size and shape of the seal member 430 and the guide sheath 410 are similar). Furthermore, the seal member 430 can be formed from any suitable material such as, for example, a biocompatible thermoplastic or the like. In some embodiments, the seal member 430 can be pliable.

Figure 17:
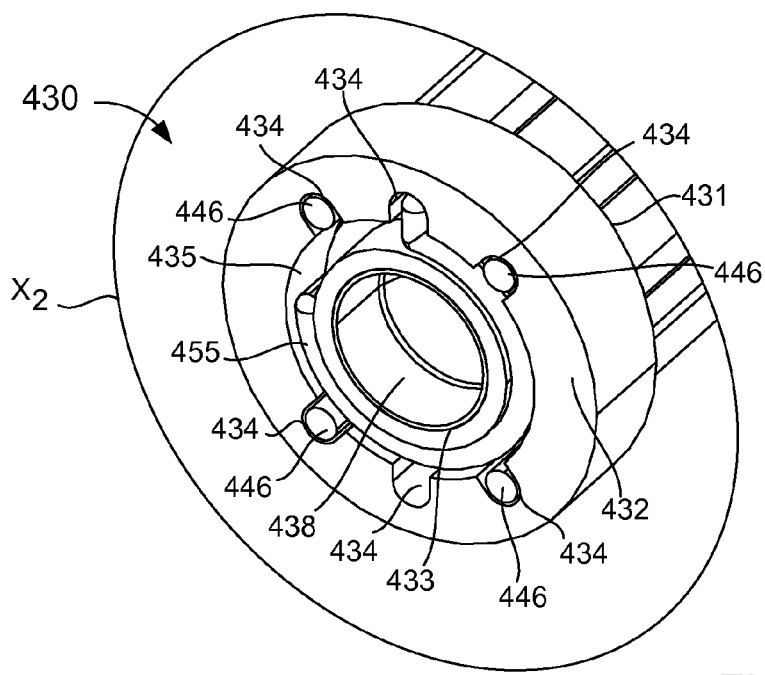
FIG. 17 is an enlarged perspective view of a portion of the endoleak repair device of FIG. 13, identified as region $X_2$ in FIG. 15.

As shown in FIG. 17, the seal member 430 includes a proximal end portion 431 and a distal end portion 432 and defines a valve opening 433 and a set of apertures or lumens 434 therethrough. The valve opening 433 can receive a hemostatic valve 438 (also referred to herein as "valve"). More specifically, a set of walls defining the valve opening 433 and the valve 438 can form a friction fit that defines a fluidic seal. The valve 438 can be any suitable configuration. For example, in some embodiments, the valve 438 can be a one-way valve that can receive at least a portion of a cannula and/or a trocar while preventing a flow of a fluid, as described in further detail herein.

The apertures 434 of the seal member 430 can each receive one of the coupling members 446 and the retention member 455. Expanding further, each of the coupling members 446 can be movably disposed within a different one of the apertures 434 and the retention member 455 can be movably disposed within two of the apertures 434. In this manner, both the coupling members 446 and the retention member 455 can be moved between a first position and a second position relative to the seal member 430, as described in further detail herein.

The seal member 430 is further configured to define a groove 435 that can receive a portion of the retention member 455. For example, as shown in FIG. 17, the retention member 455 can pass through one of the apertures 434 and coil or wrap along a path defined by the groove 435 and pass through a different aperture 434. In this manner, the retention member 455 can be disposed within the groove 435 and in contact with a proximal surface of the seal member 430 to at least temporarily retain the seal member 430 adjacent to the guide sheath 410. The retention member 455 can be any suitable configuration and can be formed from any suitable material. For example, in some embodiments, the retention member 455 can be a nylon thread or the like. In some embodiments, the retention member 455 can be formed with, for example, PTFE, silk or any other suture or graft material, or can be formed with a thin stainless steel wire. In this manner, the retention member 455 can be sufficiently flexible to be looped (e.g., wound, threaded, etc.) within the groove 435 of the seal member 430 while being sufficiently strong (e.g., tensile strength) to retain the seal member 430 adjacent to the guide sheath 410.

In use, the distal end portion 412 of the guide sheath 410 can be percutaneously inserted into the common femoral artery and guided to a previously placed endoluminal graft (ELG) within the artery (e.g., at a location of an aneurysm sac). Once at an endoleak location (e.g., as verified with image guidance techniques such as fluoroscopy or the like), the user can manipulate the distal rotation member 469 of the handle 460 by rotating the distal rotation member 469 in the direction of the arrow AA in FIG. 18. As the distal rotation member 469 rotates in the AA direction, the threaded inner surface 470 of the distal rotation member 469 engages the threaded outer surface 472 of the distal shuttle 471. Thus, the distal shuttle 471 is advanced along the threaded inner surface 470 in the direction of the arrow BB. Moreover, with the shuttle 471 disposed about the alignment rods 473, the orientation of the distal shuttle 471 relative to the handle 460 is retained.

With the proximal end portion of the deflection member 456 coupled to the distal shuttle 471, the movement of the distal shuttle 471 also moves the deflection member 456 in the BB direction. Furthermore, the coupling of the distal end portion of the deflection member 456 to the engagement member 457 (FIG. 15) is such that the deflection member 456 pulls a side of the guide sheath 410 (e.g., the side of the guide sheath defining the secondary lumen 414 in which the deflection member 456 is disposed) in the BB direction. Expanding further, by exerting a force on the side of the guide sheath 410 (e.g., as transferred by the engagement member 457), the distal end portion 412 of the guide sheath 410 is deflected in the direction of the arrow CC as shown in FIG. 18, thereby placing the repair device 400 in a deflected second configuration.

In some embodiments, the deflection of the guide sheath 410 can be such that the distal end portion 412 is placed in a substantially perpendicular position relative to a wall of the ELG. Moreover, with the distal end portion 412 deflected, the distal end portion 412 can be placed adjacent to the wall of the ELG such that the seal member 430 is placed in contact with the wall of the ELG. In this manner, the user can manipulate the proximal rotation member 474 of the handle 460 by rotating the proximal rotation member 474 in the direction of the arrow DD shown in FIG. 19. As the proximal rotation member 474 rotates in the DD direction, the threaded inner surface 475 of the proximal rotation member 474 engages the threaded outer surface 477 of the proximal shuttle 476. Thus, the proximal shuttle 476 is advanced along the threaded inner surface 475 in the direction of the arrow EE. Moreover, with the shuttle 476 disposed about the alignment rods 473, the orientation of the proximal shuttle 476 relative to the handle 460 can be retained.

With the proximal end portion of the push rods 440 coupled to the proximal shuttle 476, the movement of the proximal shuttle 476 also moves the push rods 440 in the EE direction. In this manner, the distal end portion of the push rods 440 and the coupling members 446 can be collectively moved relative to the distal end portion 412 of the guide sheath 410, as indicated by the arrow FF in FIG. 19. Moreover, with the seal member 430 in contact with the wall of the ELG, the movement of the seal member 430 can be limited. Thus, the coupling members 446 can be moved from their first position relative to the seal member 430 (e.g., as shown in FIG. 20) to their second position relative to the seal member 430 (e.g., as shown in FIG. 21).

As shown, at least a distal end portion 448 (also referred to herein as a "second coupling portion") of the coupling members 446 are advanced beyond the distal end portion 432 of the seal member 430 to puncture the wall of the ELG, as indicated by the arrow GG in FIG. 21. Furthermore, by advancing the coupling members 446 beyond the seal member 430, at least the distal end portion 448 of the coupling members 446 is substantially unconstrained (e.g., not constrained by the walls defining the secondary lumen 414 and/or by the walls defining the apertures 434 of the seal member 430), thus, at least the distal end portion 448 of the coupling members 446 can move from a first configuration to a second configuration. For example, as described above, the coupling members 446 can be formed with a shape memory alloy (e.g., nitinol), such that the distal end portion 448 of the coupling members 446 can assume a coil when unconstrained, as shown in FIG. 21. While shown as assuming a coiled configuration, in other embodiments, the coupling members 446 can be configured to assume any suitable shape when unconstrained such as, for example, a hook or tab.

When in the second configuration, at least the distal end portion 448 of the coupling members 446 can be in contact with an outer surface of the ELG. Furthermore, with the distal end portion 432 of the seal member 430 in contact with the inner surface of the ELG, the coupling members 446 can couple the seal member 430 to the ELG. For example, when in the second configuration, the coupling members 446 and the distal end portion 432 of the seal member 430 can exert a compressive force on the wall of the ELG, thereby coupling the seal member 430 to the ELG. With the seal member 430 coupled to the ELG wall, a cannula (with or without a trocar) can be inserted into the proximal port 465 of the handle and advanced within the lumen 413 of the guide sheath 410 towards the distal end portion 412.

The cannula and/or the trocar (not shown in FIGS. 13-23) can be advanced through the hemostatic valve 438 included in the seal member 430 (thereby placing the valve 438 in the open configuration) to allow the trocar to puncture the wall of the ELG. In this manner, a portion of the cannula and/or trocar can be disposed within the aneurysm sac. With the cannula and/or trocar at least partially disposed within the aneurysm sac, the cannula can be used to deliver an embolic treatment agent to a type 2 endoleak site. For example, in some embodiments, the cannula can deliver coils, glues, thrombin, fibrin, procoagulants, onyx, and/or any other suitable material. In some embodiments, the delivered material fills the area of the sac previously filled by pooling blood and at least a portion of the lumbar and/or inferior mesenteric arteries can be embolized, thus, sealing the type 2 endoleak.

In some embodiments, the trocar and/or the cannula can be retracted prior to the delivery of the embolic agent. For example, in some embodiments, the trocar can be advanced in a distal direction to puncture the ELG and to place at least a distal end of the cannula into the aneurysm sac. The trocar can then be refracted in the proximal direction relative to the cannula prior to the delivery of the embolic agent. In other embodiments, the cannula can be configured to puncture the ELG wall (e.g., can include a sharpened distal end). Therefore, in such embodiments, the trocar need not be used.

In some embodiments, the cannula and the trocar can both be retracted through proximal port 465 of the handle 460 after puncturing the ELG. In such an embodiment, after the cannula and trocar are retracted through the port 465, a separate delivery device can be inserted through the lumen 413 and through the valve 438 and used to deliver the embolic agent.

After the treatment is delivered, the cannula (and the trocar) can be retracted to a proximal position relative to the distal end portion 412 of the guide sheath 410. For example, in some embodiments, at least a portion of the cannula (and the trocar) can remain disposed within the lumen 413 of the guide sheath 410. In other embodiments, the cannula can be retracted through the proximal port 465 of the handle 460. With the cannula and trocar retracted, the hemostatic valve 438 can move to the closed configuration to prevent a flow of a fluid through the valve 438, thus the seal member 430 can seal the hole produced by the trocar puncturing the ELG wall.

With the treatment delivered to the leak site and with the seal member 430 sealing the hole in the wall of the ELG, the guide sheath 410 can be decoupled from the seal member 430 to place the repair device 400 in the fourth configuration. For example, a user can manipulate the retention mechanism 478 of the handle 460 by rotating the threaded cap 480 relative to the threaded base 479, as indicated by the arrow HH shown in FIG. 22. In this manner, the threaded cap 478 can be removed from the threaded base 479 to allow access to the retention member 455. Thus, a user can engage the retention member 455 to move the retention member 455 in the proximal direction, as indicated by the arrow II in FIG. 23. As shown, the proximal movement of the retention member 455 is such that the retention member 455 is unwound from the seal member 430 (e.g., the retention member 455 is removed from the groove 435 defined by the seal member 430).

With the retention member 455 decoupled from the seal member 430, the repair device 400 can be decoupled from the seal member 430 by moving the repair device 400 in the II direction. In this manner, the push rods 440 can be moved in a proximal direction relative to the coupling members 446 thereby decoupling the seal member 430 from the repair device 400. Once decoupled, the repair device 400 can be retracted through the common femoral artery and the seal member 430 can remain coupled to the ELG wall, thereby sealing the hole formed in the ELG.

Figure 24:
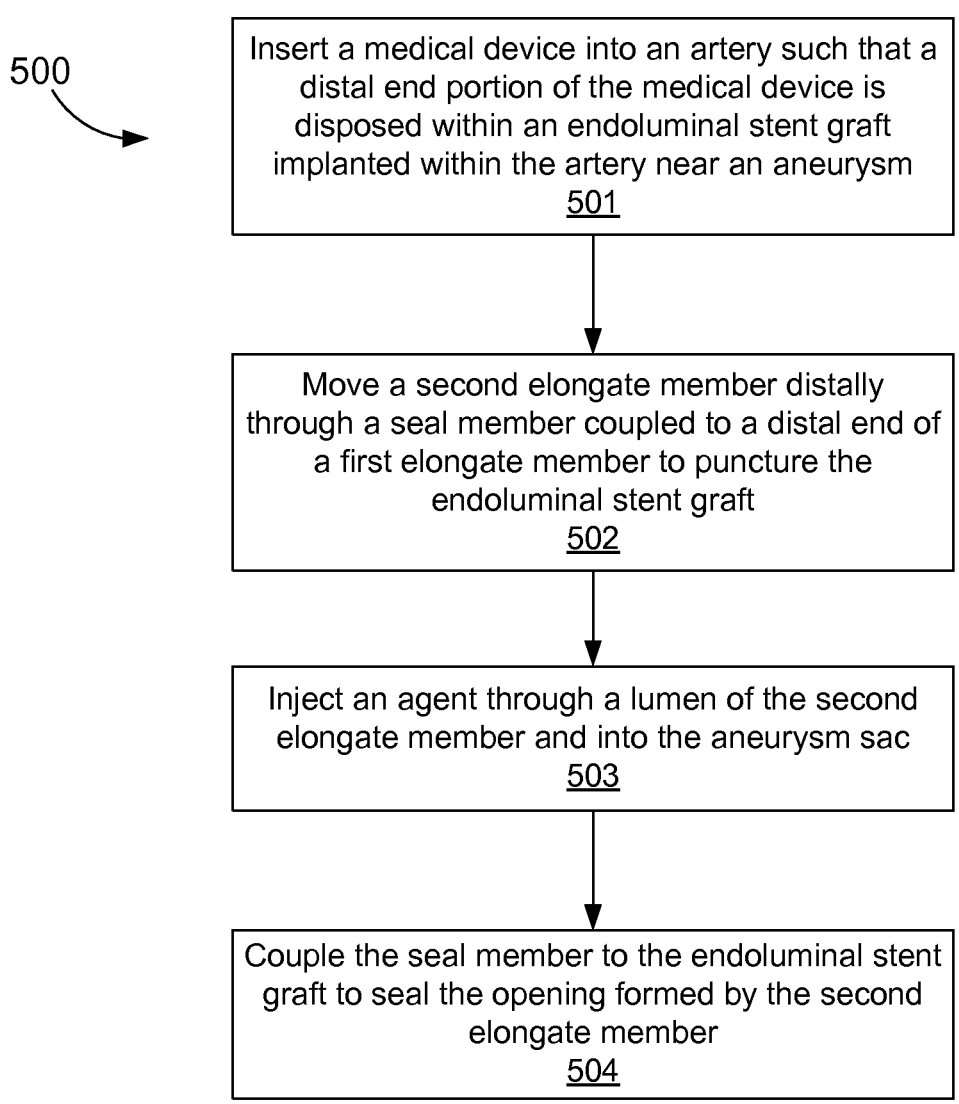
FIG. 24 is a flowchart illustrating a method of treating a type 2 endoleak, according to an embodiment.

Referring now to FIG. 24, a flowchart illustrates a method 500 for repairing a type 2 endoleak, according to an embodiment. The method 500 includes inserting a medical device (e.g., repair device 100, 200, 300, or 400) into an artery of a patient such that a distal end portion of the medical device is disposed within an endoluminal stent graft (ELG) implanted within the artery near an aneurysm, at 501. The medical device can be, for example, substantially similar to the repair device 400 described above with reference to FIGS. 13-23. In this manner, the medical device can include a first elongate member that defines a lumen (e.g., guide sheath 410) and a second elongate member (e.g., a cannula and trocar) movably disposed within the lumen. In some embodiments, when the distal end portion of the medical device is disposed within the ELG, the first elongate member can be moved from a first configuration in which the distal end portion is substantially linear to a second configuration in which the distal end portion is disposed at an angle relative to a remaining portion of the first elongate member. In this manner, the distal end portion of the first elongate member can be disposed, for example, adjacent to a wall of the ELG.

At 502, the second elongate member is moved in a distal direction through a seal member (e.g., 130, 230, 330, or 430) that is coupled to a distal end portion of the first elongate member. For example, in some embodiments, the seal member (e.g., similar to or the same as the seal member 430) includes a valve that can be moved to an open configuration by moving the second elongate member therethrough. The distal movement of the second elongate member through the seal member is such that a distal end portion of the second elongate member punctures the ELG. For example, in some embodiments, a trocar can be advanced relative to a cannula (e.g., the second elongate member) to puncture the ELG forming an opening in the ELG and at least partially disposing the second elongate member within the aneurysm.

An agent is delivered through the lumen of the first elongate member and into the aneurysm sac, at 503. For example, in some embodiments, the second elongate member can be refracted and a delivery device can be inserted into the lumen of the first elongate member and used to deliver the agent (e.g., an embolic agent) into the aneurysm. In other embodiments, the second elongate member can remain at least partially disposed within the aneurysm sac and the agent can be pumped or otherwise moved through a lumen defined by the second elongate member. For example, if the second elongate member includes a cannula and a trocar, the trocar can be retracted and the agent can be delivered through the lumen of the cannula and into the aneurysm.

After the agent has been delivered to the aneurysm, at 504, the seal member can be coupled to the ELG to seal the opening formed by the second elongate member. For example, in some embodiments, the second elongate member can be retracted to a proximal position relative to the seal member such that the valve included in the seal member can move to a closed configuration. The seal member can then be coupled to the ELG to seal the hole formed by the second elongate member. For example, in some embodiments, the medical device can include at least one push rod configured to move a coupling portion of a coupling member in a distal direction such that the a coupling portion is disposed outside of the ELG. In such embodiments, the coupling portion can be configured to assume a biased configuration that couples the seal member to the ELG. With the seal member coupled to the ELG, the medical device can be decoupled from the seal member and the medical device can be removed from the artery while the seal member remains coupled to the ELG.

Figure 25:
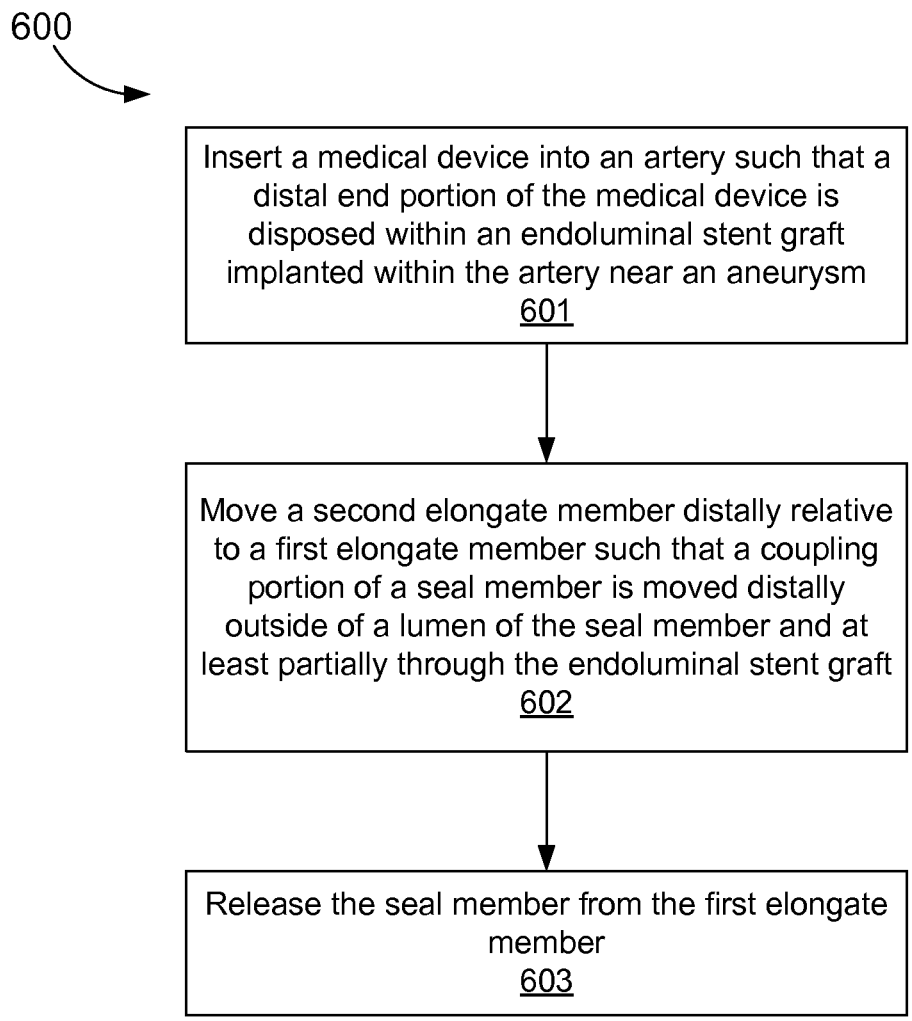
FIG. 25 is a flowchart illustrating a method of treating a type 2 endoleak, according to an embodiment.

FIG. 25 is a flowchart illustrating a method 600 for treating a type 2 endoleak, according to an embodiment. The method 600 includes inserting a medical device (e.g., 100, 200, 300, or 400) into an artery of a patient such that a distal end portion of the medical device is disposed within an endoluminal stent graft (ELG) implanted within the artery near an aneurysm, at 601. The medical device can be, for example, substantially similar to the repair device 400 described above with reference to FIGS. 13-23. In this manner, the medical device can include a first elongate member (e.g., similar to the guide sheath 410) that defines a lumen, a second elongate member (e.g., similar to one of the push rods 440) movably disposed within the lumen, and a seal member (e.g., similar to the seal member 430) coupled to a distal end portion of the first elongate member.

In some embodiments, when the distal end portion of the medical device is disposed within the ELG, the first elongate member can be moved from a first configuration in which the distal end portion is substantially linear, to a second configuration in which the distal end portion is disposed at an angle relative to a remaining portion of the first elongate member. In this manner, the distal end portion of the first elongate member can be disposed, for example, adjacent to a wall of the ELG. In some embodiments, the distal end portion of the first elongate member can be moved to place the seal member in contact with the wall of the ELG. In some embodiments, with the seal member in contact with the ELG, a third elongate (e.g., a cannula and trocar) can be moved through a second lumen of the first elongate member in a distal direction and through the seal member. For example, in some embodiments, the seal member can include a valve that can be moved to an open configuration by moving the second elongate member therethrough. The distal movement of the third elongate member through the seal member is such that a distal end portion of the third elongate member punctures the ELG and forms an opening through which at least a portion of the third elongate member can be disposed within the aneurysm. In this manner, a sealing agent can be injected through the opening in the ELG and into the aneurysm sac.

At 602, the second elongate member is moved distally relative to the first elongate member such that a coupling portion of a coupling member is moved in a distal direction and is disposed outside of a lumen defined by the seal member and at least partially through the ELG. For example, in some embodiments, the medical device can include a coupling member that includes a coupling portion (e.g., similar to the coupling portion 251 described above with reference to FIGS. 2-10). In this manner, the coupling portion can assume a biased configuration that couples the seal member to the ELG.

With the seal member coupled to the ELG, the seal member is released from the first elongate member, at 603. For example, in some embodiments, the medical device can include a retention member (e.g., similar to the retention member 455) that couples the seal member to the distal end portion of the first elongate member. In such embodiments, the retention member can be moved in a proximal direction to release the seal member from the first elongate member. In some embodiments, the releasing of the seal member from the first elongate member includes decoupling a second coupling portion of a coupling member (e.g., 246, 346, or 446) from the second elongate member. For example, in some embodiments, the retention member can exert a force that retains the second coupling portion coupled to the second elongate member. Thus, when the retention member is decoupled from the seal member, the second coupling portion can be decoupled from the second elongate member. With the medical device decoupled from the seal member, the medical device can be removed from the artery while the seal member remains coupled to the ELG.

In some embodiments, the devices described herein can be used to cannulate a renal artery or superior mesenteric artery (SMA) in those instances when an ELG is placed in a patient with a short proximal neck. That is, the ELG is placed high in the aorta and the fabric of the ELG covers a renal artery or the SMA. In such instances, a trocar included in the device can be used to access the artery through the graft material (e.g., pierce the graft material to gain access to the artery). In this manner, a guide wire can be placed and a stent graft or bare stent can be inserted over the guide wire into the renal or SMA artery re-establishing blood flow to the kidney or bowel.

In alternative embodiments, rather than sealing the opening formed in the ELG wall by the cannula and/or trocar with a seal member as described above, the opening can be closed using sutures. For example, an endoleak repair device as described herein can include a suturing device or mechanism that can be used to suture the opening. In some embodiments, a separate suturing device can be used to suture the opening.

In some embodiments, an endoleak repair device such as, for example, the endoleak repair device 400 shown and described with reference to FIGS. 13-23, can include a probe configured to identify the location of an endoleak. For example, in some embodiments, a distal end portion of an endoleak repair device can include an intravascular ultrasound (IVUS) probe. In such embodiments, the IVUS probe can be configured to provide for visualization of the endoleak before puncturing the endoluminal graft, thus, ensuring the correct placement of the endoluminal repair device. In some embodiments, the IVUS probe can be configured to provide visualization of, for example, the location of the renal or mesenteric artery. In some embodiments, the visualization of the renal or mesenteric artery can facilitate stenting the renal or mesenteric artery, as described above. In some embodiments, the device can include one or more radiopaque markers such that the device is visible using an external imaging source.

In some embodiments, an endoleak repair device can be configured to deliver an embolic agent and a pressure-sensing device. In this manner, the pressure-sensing device can be implanted into the aneurysm sac to monitor the pressure within the aneurysm sac. In such embodiments, a secondary device (e.g., a computer including at least a processor and a memory) can be configured to monitor a signal produced by the pressure-sensing device.

While the embodiments have been described above as repairing a type 2 endoleak, in other embodiments, any of the embodiments described herein can be used in a preventative manner. For example, in some embodiments, the devices described herein can be used directly after and/or partially coincidentally with the placement of an endoluminal stent graft. In such embodiments, the device can deliver an embolic agent to the aneurysm sac configured to at least partially regulate the pressure within the aneurysm sac. In this manner, the likelihood of developing a type 2 endoleak can be reduced.

While various embodiments have been described above, it should be understood that they have been presented by way of example only, and not limitation. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or schematics described above indicate certain events and/or procedures occurring in certain order, the ordering of certain events and/or flow patterns may be modified. Additionally, certain of the steps may be performed concurrently in a parallel process when possible, as well as performed sequentially as described above.

In addition, the specific configurations of the various components can also be varied. For example, the size and specific shape of the various components can be different from the embodiments shown, while still providing the functions as described herein.

What is claimed is:

1. A method, comprising: inserting a medical device into an artery such that a distal end portion of the medical device is disposed within an endoluminal stent graft implanted within the artery near an aneurysm, the medical device including a first elongate member defining a lumen and a second elongate member movably disposable within the lumen; moving the second elongate member distally through a seal member coupled to a distal end portion of the first elongate member such that a distal end of the second elongate member punctures the endoluminal stent graft forming an opening in the endoluminal stent graft and is disposed at least partially within the aneurysm; injecting an agent through a lumen of the second elongate member and into the aneurysm sac; and directly coupling the seal member to the endoluminal stent graft to seal the opening formed by the second elongate member.

2. The method of claim 1, further comprising:
prior to the moving the second elongate member, actuating the first elongate member to move from a first configuration in which a distal end portion of the first elongate is substantially linear to a second configuration in which the distal end portion of the first elongate member is disposed at an angle relative to a remaining portion of the first elongate member.

3. The method of claim 1, wherein the coupling the seal member to the endoluminal stent graft includes moving distally a push rod coupled to a coupling member such that a coupling portion of the coupling member is moved outside of a lumen of the seal member and assumes a biased configuration.

4. The method of claim 1, wherein the second elongate member includes a trocar movably disposable within the lumen of the second elongate member, the method further comprising:
prior to the injecting, removing the trocar from the lumen of the second elongate member.

5. The method of claim 1, further comprising:
prior to the injecting, removing the second elongate member from the lumen of the first elongate member; and
inserting into the lumen of the first elongate member a device configured to communicate the sealing agent such that a distal end of the device is disposed through the opening formed in the endoluminal stent graft and within the aneurysm.

6. A method, comprising: inserting a medical device into an artery such that a distal end portion of the medical device is disposed within an endoluminal stent graft implanted within the artery near an aneurysm, the medical device including a first elongate member defining a lumen, a second elongate member disposed within the lumen, and a seal member releasably coupled to a distal end portion of the first elongate member with a coupling member; moving the second elongate member distally relative to the first elongate member such that a coupling portion of the coupling member is moved distally outside of a lumen of the seal member and at least partially through the endoluminal stent graft, the coupling portion configured to assume a biased configuration when moved outside the lumen of the seal member such that the coupling portion directly couples the seal member to the endoluminal stent; and releasing the seal member from the first elongate member.

7. The method of claim 6, further comprising:
prior to the moving the second elongate member, actuating the first elongate member to move from a first configuration in which a distal end portion of the first elongate is substantially linear to a second configuration in which the distal end portion of the first elongate member is disposed at an angle relative to a remaining portion of the first elongate member.

8. The method of claim 6, wherein the lumen is a first lumen, the first elongate member defines a second lumen, the method further comprising:
prior to the moving the second elongate member, moving distally a third elongate member within the second lumen such that a distal end of the third elongate member punctures the endoluminal stent graft and forms an opening in the endoluminal stent graft.

9. The method of claim 6, wherein the lumen is a first lumen, the first elongate member defines a second lumen, the method further comprising:

prior to the moving the second elongate member, moving distally a third elongate member within the second lumen such that a distal end of the third elongate member punctures the endoluminal stent graft and forms an opening in the endoluminal stent graft and a distal end portion of the third elongate member is disposed within the aneurysm; and injecting a sealing agent through a lumen of the third elongate member and into the aneurysm.

10. The method of claim 6, wherein the lumen is a first lumen, the first elongate member defines a second lumen, the method further comprising:

prior to the moving the second elongate member, moving distally a third elongate member within the second lumen such that a distal end of the third elongate member punctures the endoluminal stent graft and forms an opening in the endoluminal stent graft;

inserting into the second lumen of the first elongate member a device configured to communicate a sealing agent such that a distal end of the device is disposed through the opening formed in the endoluminal stent graft and within the aneurysm; and injecting a sealing agent into the aneurysm via the device.

11. The method of claim 6, wherein the coupling portion of the coupling member is a first coupling portion, the releasing the seal member includes detaching a second coupling portion of the coupling member from a distal end portion of the second elongate member.

12. The method of claim 6, further comprising:

after the releasing, collectively removing the first elongate member and the second elongate member from the artery.

* * * * *